US009292187B2

(12) United States Patent
Whitman et al.

(10) Patent No.: US 9,292,187 B2
(45) Date of Patent: Mar. 22, 2016

(54) SYSTEM, METHOD AND GRAPHICAL USER INTERFACE FOR DISPLAYING AND CONTROLLING VISION SYSTEM OPERATING PARAMETERS

(71) Applicant: Cognex Corporation, Natick, MA (US)

(72) Inventors: Steven M. Whitman, Danville, NH (US); Robert Tremblay, Grafton, MA (US); Carroll McNeill Arbogast, Jr., Needham, MA (US)

(73) Assignee: COGNEX CORPORATION, Natick, MA (US)

( * ) Notice: Subject to any disclaimer, the term of this patent is extended or adjusted under 35 U.S.C. 154(b) by 266 days.

(21) Appl. No.: 14/106,568

(22) Filed: Dec. 13, 2013

(65) Prior Publication Data

US 2014/0177979 A1 Jun. 26, 2014

Related U.S. Application Data

(63) Continuation-in-part of application No. 13/565,609, filed on Aug. 2, 2012, which is a continuation-in-part of application No. 12/758,455, filed on Apr. 12, 2010, now Pat. No. 8,582,925, which is a continuation of application No. 10/988,120, filed on Nov. 12, 2004, now Pat. No. 7,720,315.

(51) Int. Cl.
  *G06F 3/0484* (2013.01)
  *G06F 3/0481* (2013.01)
  *G01N 21/90* (2006.01)
(52) U.S. Cl.
  CPC .......... *G06F 3/04847* (2013.01); *G06F 3/0481* (2013.01); *G06F 3/04842* (2013.01); *G01N 21/90* (2013.01); *G05B 2219/32128* (2013.01)
(58) Field of Classification Search
  CPC .................................. G06F 3/04847

USPC ......................................................... 715/764
See application file for complete search history.

(56) References Cited

U.S. PATENT DOCUMENTS

| 4,214,265 A | 7/1980 | Olesen |
| 4,292,666 A | 9/1981 | Hill et al. |

(Continued)

FOREIGN PATENT DOCUMENTS

| DE | 10012715 | 9/2000 |
| DE | 10040563 | 2/2002 |

(Continued)

OTHER PUBLICATIONS

Cognex Corporation, "3000/4000/5000 Vision Tools, Revision 7.6, Chapter 10", 1996, pp. 590-0136, Published in: US.

(Continued)

*Primary Examiner* — Reza Nabi
(74) *Attorney, Agent, or Firm* — Loginov IP

(57) ABSTRACT

A graphical user interface (GUI) display and GUI-based system for displaying and controlling vision system operating parameters of a contour sensor comprises an automated region of interest graphic image applied to a discrete region of a selected image in response to a single click by a user at the discrete region of the selected image, the selected image selected from a window on the GUI display containing a plurality of captured images of the object. At least one automated operating parameter is generated automatically in response to the single click by the user at the discrete region of the selected image to determine whether a contour of interest is in the automated ROI graphic image. The GUI also provides a contour graphic image that outlines the contour of interest to demonstrate whether the contour of interest is in (present or at the correct position within) the automated ROI graphic image.

21 Claims, 12 Drawing Sheets

(56) References Cited

U.S. PATENT DOCUMENTS

| | | | |
|---|---|---|---|
| 4,384,195 A | 5/1983 | Nosler | |
| 4,647,979 A | 3/1987 | Urata | |
| 4,679,075 A | 7/1987 | Williams et al. | |
| 4,847,772 A | 7/1989 | Michalopoulos et al. | |
| 4,916,640 A | 4/1990 | Gasperi | |
| 4,962,538 A | 10/1990 | Eppler et al. | |
| 4,972,494 A | 11/1990 | White et al. | |
| 5,018,213 A | 5/1991 | Sikes | |
| 5,040,056 A | 8/1991 | Sager et al. | |
| 5,121,201 A | 6/1992 | Seki | |
| 5,146,510 A | 9/1992 | Cox et al. | |
| 5,164,998 A | 11/1992 | Reinsch et al. | |
| 5,177,420 A | 1/1993 | Wada | |
| 5,184,217 A | 2/1993 | Doering | |
| 5,198,650 A | 3/1993 | Wike et al. | |
| 5,210,798 A | 5/1993 | Ekchian et al. | |
| 5,233,541 A | 8/1993 | Corwin et al. | |
| 5,262,626 A | 11/1993 | Goren et al. | |
| 5,271,703 A | 12/1993 | Lindqvist et al. | |
| 5,286,960 A | 2/1994 | Longacre, Jr. et al. | |
| 5,298,697 A | 3/1994 | Suzuki et al. | |
| 5,317,645 A * | 5/1994 | Perozek | G06M 11/00 209/522 |
| 5,345,515 A | 9/1994 | Nishi et al. | |
| 5,365,596 A | 11/1994 | Dante et al. | |
| 5,420,409 A | 5/1995 | Longacre, Jr. et al. | |
| 5,476,010 A | 12/1995 | Fleming et al. | |
| 5,481,712 A | 1/1996 | Silver et al. | |
| 5,500,732 A | 3/1996 | Ebel et al. | |
| 5,562,788 A | 10/1996 | Kitson et al. | |
| 5,581,625 A | 12/1996 | Connell et al. | |
| 5,657,050 A | 8/1997 | McCambridge et al. | |
| 5,687,249 A | 11/1997 | Kato | |
| 5,717,834 A * | 2/1998 | Werblin | G06N 3/063 706/16 |
| 5,734,742 A * | 3/1998 | Asaeda | G01N 21/88 382/107 |
| 5,742,037 A | 4/1998 | Scola et al. | |
| 5,751,831 A | 5/1998 | Ono | |
| 5,802,220 A | 9/1998 | Black et al. | |
| 5,809,161 A | 9/1998 | Auty et al. | |
| 5,825,483 A | 10/1998 | Michael et al. | |
| 5,838,592 A | 11/1998 | Spratt | |
| 5,852,669 A | 12/1998 | Eleftheriadis et al. | |
| 5,872,354 A | 2/1999 | Hanson | |
| 5,917,602 A | 6/1999 | Bonewitz et al. | |
| 5,929,418 A | 7/1999 | Ehrhart et al. | |
| 5,932,862 A | 8/1999 | Hussey et al. | |
| 5,937,096 A | 8/1999 | Kawai | |
| 5,942,741 A | 8/1999 | Longacre et al. | |
| 5,943,432 A | 8/1999 | Gilmore et al. | |
| 5,960,097 A | 9/1999 | Pfeiffer et al. | |
| 5,960,125 A | 9/1999 | Michael et al. | |
| 5,966,457 A | 10/1999 | Lemelson | |
| 6,046,764 A | 4/2000 | Kirby et al. | |
| 6,049,619 A | 4/2000 | Anandan et al. | |
| 6,061,471 A | 5/2000 | Coleman | |
| 6,072,494 A | 6/2000 | Nguyen | |
| 6,072,882 A | 6/2000 | White et al. | |
| 6,075,882 A | 6/2000 | Mullins et al. | |
| 6,078,251 A | 6/2000 | Landt et al. | |
| 6,088,467 A | 7/2000 | Sarpeshkar et al. | |
| 6,115,480 A | 9/2000 | Washizawa | |
| 6,158,661 A | 12/2000 | Chadima, Jr. et al. | |
| 6,160,494 A | 12/2000 | Sodi et al. | |
| 6,161,760 A | 12/2000 | Marrs | |
| 6,169,535 B1 | 1/2001 | Lee | |
| 6,169,600 B1 | 1/2001 | Ludlow | |
| 6,173,070 B1 * | 1/2001 | Michael | G06K 9/00201 382/145 |
| 6,175,644 B1 * | 1/2001 | Scola | G01N 21/8851 117/201 |
| 6,175,652 B1 * | 1/2001 | Jacobson | C30B 15/26 117/14 |
| 6,184,924 B1 | 2/2001 | Schneider et al. | |
| 6,215,892 B1 | 4/2001 | Douglass et al. | |
| 6,282,462 B1 | 8/2001 | Hopkins | |
| 6,285,787 B1 | 9/2001 | Kawachi et al. | |
| 6,298,176 B2 | 10/2001 | Longacre, Jr. et al. | |
| 6,301,610 B1 | 10/2001 | Ramser et al. | |
| 6,333,993 B1 * | 12/2001 | Sakamoto | G06T 7/0081 358/464 |
| 6,346,966 B1 * | 2/2002 | Toh | H04N 5/2354 348/340 |
| 6,347,762 B1 | 2/2002 | Sims et al. | |
| 6,360,003 B1 | 3/2002 | Doi et al. | |
| 6,396,517 B1 | 5/2002 | Beck et al. | |
| 6,396,949 B1 | 5/2002 | Nichani | |
| 6,408,429 B1 | 6/2002 | Marrion et al. | |
| 6,446,868 B1 | 9/2002 | Robertson et al. | |
| 6,483,935 B1 | 11/2002 | Rostami et al. | |
| 6,487,304 B1 | 11/2002 | Szeliski | |
| 6,525,810 B1 | 2/2003 | Kipman | |
| 6,526,156 B1 | 2/2003 | Black et al. | |
| 6,539,107 B1 | 3/2003 | Michael et al. | |
| 6,540,685 B1 | 4/2003 | Rhoads et al. | |
| 6,542,692 B1 | 4/2003 | Houskeeper | |
| 6,545,705 B1 | 4/2003 | Sigel et al. | |
| 6,549,647 B1 | 4/2003 | Skunes et al. | |
| 6,573,929 B1 | 6/2003 | Glier et al. | |
| 6,580,510 B2 | 6/2003 | Yang et al. | |
| 6,580,810 B1 | 6/2003 | Yang et al. | |
| 6,587,122 B1 | 7/2003 | King | |
| 6,597,381 B1 | 7/2003 | Eskridge et al. | |
| 6,604,174 B1 | 8/2003 | Gerst et al. | |
| 6,608,930 B1 | 8/2003 | Agnihotri et al. | |
| 6,618,074 B1 | 9/2003 | Seeley et al. | |
| 6,621,571 B1 | 9/2003 | Maeda et al. | |
| 6,625,317 B1 | 9/2003 | Gaffin et al. | |
| 6,628,805 B1 | 9/2003 | Hansen et al. | |
| 6,629,642 B1 | 10/2003 | Swartz et al. | |
| 6,646,244 B2 | 11/2003 | Aas et al. | |
| 6,668,075 B1 | 12/2003 | Nakamura | |
| 6,677,852 B1 | 1/2004 | Landt | |
| 6,681,151 B1 | 1/2004 | Weinzimmer et al. | |
| 6,714,213 B1 | 3/2004 | Lithicum et al. | |
| 6,741,977 B1 | 5/2004 | Nagaya et al. | |
| 6,753,876 B2 | 6/2004 | Brooksby et al. | |
| 6,761,316 B2 | 7/2004 | Bridgelall | |
| 6,766,414 B2 | 7/2004 | Francis | |
| 6,774,917 B1 | 8/2004 | Foote et al. | |
| 6,816,063 B2 | 11/2004 | Kubler | |
| 6,817,982 B2 | 11/2004 | Fritz et al. | |
| 6,825,856 B1 | 11/2004 | Fazzio et al. | |
| 6,891,570 B2 | 5/2005 | Tantalo et al. | |
| 6,919,793 B2 | 7/2005 | Heinrich | |
| 6,943,842 B2 | 9/2005 | Stavely et al. | |
| 6,944,584 B1 | 9/2005 | Tenney et al. | |
| 6,947,151 B2 | 9/2005 | Fujii et al. | |
| 6,973,209 B2 * | 12/2005 | Tanaka | G01N 21/94 348/125 |
| 6,985,827 B2 | 1/2006 | Williams et al. | |
| 6,987,528 B1 | 1/2006 | Nagahisa et al. | |
| 6,997,556 B2 | 2/2006 | Pfleger | |
| 6,999,625 B1 | 2/2006 | Nelson | |
| 7,062,071 B2 | 6/2006 | Tsujino et al. | |
| 7,066,388 B2 | 6/2006 | He | |
| 7,070,099 B2 | 7/2006 | Patel | |
| 7,085,401 B2 | 8/2006 | Averbuch et al. | |
| 7,088,387 B1 | 8/2006 | Freeman et al. | |
| 7,088,846 B2 | 8/2006 | Han et al. | |
| 7,097,102 B2 | 8/2006 | Patel et al. | |
| 7,175,090 B2 | 2/2007 | Nadabar | |
| 7,181,066 B1 | 2/2007 | Wagman | |
| 7,227,978 B2 | 6/2007 | Komatsuzaki et al. | |
| 7,266,768 B2 | 9/2007 | Ferlitsch et al. | |
| 7,274,808 B2 | 9/2007 | Baharav et al. | |
| 7,280,685 B2 | 10/2007 | Beardsley et al. | |
| 7,604,174 B2 | 10/2009 | Gerst et al. | |
| 7,636,449 B2 * | 12/2009 | Mirtich | G06F 9/4443 382/100 |
| 7,657,081 B2 | 2/2010 | Blais et al. | |
| 7,720,315 B2 * | 5/2010 | Mirtich | G06F 3/04847 382/141 |

(56) References Cited

U.S. PATENT DOCUMENTS

| | | | |
|---|---|---|---|
| 7,751,625 B2 | 7/2010 | Ulrich et al. | |
| 7,832,642 B2 | 11/2010 | Sato et al. | |
| 7,984,854 B2 | 7/2011 | Nadabar et al. | |
| 8,108,176 B2 | 1/2012 | Nadabar et al. | |
| 8,127,247 B2* | 2/2012 | Tremblay | G06K 9/6253 382/149 |
| 8,249,297 B2* | 8/2012 | Silver | G06T 7/0008 382/103 |
| 8,891,852 B2* | 11/2014 | Eames | G06T 7/0004 382/141 |
| 9,092,841 B2* | 7/2015 | Silver | G06T 7/0006 |
| 9,123,093 B1* | 9/2015 | Schumacher | G06T 7/0004 |
| 2001/0042789 A1 | 11/2001 | Krichever et al. | |
| 2002/0005895 A1 | 1/2002 | Freeman et al. | |
| 2002/0037770 A1 | 3/2002 | Paul et al. | |
| 2002/0099455 A1 | 7/2002 | Ward | |
| 2002/0109112 A1 | 8/2002 | Guha et al. | |
| 2002/0122582 A1 | 9/2002 | Masuda et al. | |
| 2002/0177918 A1 | 11/2002 | Pierel et al. | |
| 2002/0181405 A1 | 12/2002 | Ying | |
| 2002/0196336 A1 | 12/2002 | Batson et al. | |
| 2002/0196342 A1 | 12/2002 | Walker et al. | |
| 2003/0062418 A1 | 4/2003 | Barber et al. | |
| 2003/0095710 A1 | 5/2003 | Tessadro | |
| 2003/0113018 A1 | 6/2003 | Nefian et al. | |
| 2003/0120714 A1 | 6/2003 | Wolff et al. | |
| 2003/0137590 A1 | 7/2003 | Barnes et al. | |
| 2003/0201328 A1 | 10/2003 | Jam et al. | |
| 2003/0219146 A1 | 11/2003 | Jepson et al. | |
| 2003/0227483 A1 | 12/2003 | Schultz et al. | |
| 2004/0122306 A1 | 6/2004 | Spoonhower et al. | |
| 2004/0148057 A1 | 7/2004 | Breed et al. | |
| 2004/0201669 A1 | 10/2004 | Guha et al. | |
| 2004/0218806 A1 | 11/2004 | Miyamoto et al. | |
| 2004/0220770 A1 | 11/2004 | Isumi et al. | |
| 2005/0173633 A1 | 8/2005 | Tanaka et al. | |
| 2005/0184217 A1 | 8/2005 | Kong et al. | |
| 2005/0226490 A1 | 10/2005 | Phillips et al. | |
| 2005/0254106 A9 | 11/2005 | Silverbrook et al. | |
| 2005/0257646 A1 | 11/2005 | Yeager | |
| 2005/0275728 A1* | 12/2005 | Mirtich | G03B 7/087 348/211.99 |
| 2005/0275831 A1* | 12/2005 | Silver | G06K 9/4609 356/237.1 |
| 2005/0275833 A1 | 12/2005 | Silver | |
| 2005/0275834 A1 | 12/2005 | Silver | |
| 2005/0276445 A1 | 12/2005 | Silver et al. | |
| 2005/0276459 A1 | 12/2005 | Eames et al. | |
| 2005/0276460 A1 | 12/2005 | Silver et al. | |
| 2005/0276461 A1 | 12/2005 | Silver et al. | |
| 2005/0276462 A1 | 12/2005 | Silver et al. | |
| 2006/0022052 A1 | 2/2006 | Patel et al. | |
| 2006/0043303 A1 | 3/2006 | Safai et al. | |
| 2006/0056732 A1 | 3/2006 | Holmes | |
| 2006/0093205 A1 | 5/2006 | Bryll et al. | |
| 2006/0107211 A1* | 5/2006 | Mirtich | G06F 3/04847 715/700 |
| 2006/0107223 A1 | 5/2006 | Mirtich et al. | |
| 2006/0131419 A1 | 6/2006 | Nunnink | |
| 2006/0133757 A1 | 6/2006 | Nunnink | |
| 2006/0146337 A1 | 7/2006 | Marshall et al. | |
| 2006/0146377 A1 | 7/2006 | Marshall et al. | |
| 2006/0223628 A1 | 10/2006 | Walker et al. | |
| 2006/0249581 A1 | 11/2006 | Smith et al. | |
| 2006/0283952 A1 | 12/2006 | Wang | |
| 2007/0009152 A1 | 1/2007 | Kanda | |
| 2007/0116357 A1 | 5/2007 | Dewaele | |
| 2007/0146491 A1* | 6/2007 | Tremblay | G06K 9/6253 348/211.99 |
| 2007/0181692 A1 | 8/2007 | Barkan et al. | |
| 2007/0225846 A1 | 9/2007 | Bogan et al. | |
| 2008/0004822 A1 | 1/2008 | Nadabar et al. | |
| 2008/0011855 A1 | 1/2008 | Nadabar | |
| 2008/0036873 A1 | 2/2008 | Silver | |
| 2008/0063245 A1 | 3/2008 | Benkley et al. | |
| 2008/0158678 A1* | 7/2008 | Costigan | G02B 7/04 359/512 |
| 2008/0166015 A1 | 7/2008 | Haering et al. | |
| 2008/0167890 A1 | 7/2008 | Pannese et al. | |
| 2008/0205714 A1 | 8/2008 | Benkley | |
| 2008/0219521 A1 | 9/2008 | Benkley | |
| 2008/0226132 A1 | 9/2008 | Gardner et al. | |
| 2008/0285802 A1 | 11/2008 | Bramblet et al. | |
| 2008/0309920 A1 | 12/2008 | Silver | |
| 2008/0310676 A1 | 12/2008 | Silver | |
| 2009/0105589 A1 | 4/2009 | Osaka et al. | |
| 2009/0121027 A1 | 5/2009 | Nadabar | |
| 2009/0154779 A1 | 6/2009 | Satyan et al. | |
| 2009/0257621 A1 | 10/2009 | Silver | |
| 2009/0273668 A1 | 11/2009 | Mirtich et al. | |
| 2010/0215245 A1 | 8/2010 | Olivan Bescos | |
| 2010/0241901 A1 | 9/2010 | Jahn et al. | |
| 2010/0241911 A1 | 9/2010 | Shih | |
| 2010/0241981 A1 | 9/2010 | Mirtich et al. | |
| 2010/0318936 A1 | 12/2010 | Tremblay et al. | |
| 2013/0074005 A1* | 3/2013 | Whitman | G06F 3/0481 715/799 |
| 2013/0110399 A1* | 5/2013 | Moss | G06F 17/18 702/3 |
| 2014/0177979 A1* | 6/2014 | Whitman | G06F 3/0481 382/311 |

FOREIGN PATENT DOCUMENTS

| | | |
|---|---|---|
| EP | 0896290 B1 | 2/1999 |
| EP | 0939382 | 9/1999 |
| EP | 0815688 | 5/2000 |
| EP | 1469420 A2 | 10/2004 |
| EP | 1734456 A1 | 12/2006 |
| GB | 2226130 | 6/1990 |
| GB | 2309078 | 7/1997 |
| JP | 60147602 A | 8/1985 |
| JP | 08-313454 | 11/1996 |
| JP | 09-178670 | 7/1997 |
| JP | 09185710 | 7/1997 |
| JP | 11-101689 A2 | 4/1999 |
| JP | 200084495 | 3/2000 |
| JP | 2000-227401 | 8/2000 |
| JP | 2000293694 | 10/2000 |
| JP | 2000298103 | 10/2000 |
| JP | 2000322450 A | 11/2000 |
| JP | 2001109884 | 4/2001 |
| JP | 2001194323 | 7/2001 |
| JP | 2002-148201 | 5/2002 |
| JP | 2002148205 A2 | 5/2002 |
| JP | 2002-214153 | 7/2002 |
| JP | 2002318202 | 10/2002 |
| JP | 2003270166 | 9/2003 |
| JP | 2004-145504 | 5/2004 |
| JP | 9288060 A2 | 12/2009 |
| WO | 9609597 | 3/1996 |
| WO | 0215120 | 2/2002 |
| WO | 02075637 | 9/2002 |
| WO | 03102859 | 12/2003 |
| WO | 2005050390 | 6/2005 |
| WO | WO-2005124317 | 6/2005 |
| WO | 2005124719 | 12/2005 |
| WO | WO-2005124709 | 12/2005 |

OTHER PUBLICATIONS

Cognex Corporation, "3000/4000/500 Vision Tools Revision 7.6, Chapter 13", 1996, pp. 590-0136, Published in: US.

Analog Devices, Inc., "ADSP-BF533 Blackfin Processor Hardware Reference, Preliminary Revision, Part No. 82-002005-01", Mar. 2003, p. 936 Publisher: Media Platforms and Services Group, Published in: Norwood, MA USA.

Analogic Computers Ltd., "Bio-inspired Real-time Very High Speed Image Processing Systems", Sep. 24, 2004, p. 3 Publisher: Analogic Computers Ltd., Published in: Budapest, Hungary.

Bi-I, "AnaLogic Computers Ltd.", 2003.

Marsh, et al., "The Application Knowledge Based Vision to Closed-Loop Control of the Injection Molding Process", 1997, pp. 605-616,

(56) References Cited

OTHER PUBLICATIONS vol. 3164, Publisher: SPIE, Faculty of Engineering, University of the West of England, Published in: GB.

Kim, et al., "Automatic Description of Complex Buildings With Multiple Images", "IEEE 0-7695-0813-8/00", 2000, pp. 155-162, Publisher: IEEE.

Baillard, et al., "Automatic Reconstruction of Piecewise Planar Models From Multipe Views", 1999, p. 2559 vol. 02, No. 2, Publisher: CVPR.

Avalon Vision Solutions, "If accuracy matters in your simplest vision application Use the Validator", 2006.

Vietze, Oliver, "Miniaturized Vision Sensors for Process Automation", Jan. 2, 2005.

Baumer Optronic, "Technische Daten", , p. 6 Published in: Baumer Optronic.

Analog Devices, Inc., "Blackfin Processor Instruction Set Reference, Revision 2.0, Part No. 82-000410-14", May 2003, p. 514 Published in: Norwood, MA USA.

Kahn, "Building Blocks for Computer Vision Systems", Dec. 1993, pp. 40-50, vol. 8, No. 6, Publisher: IEEE Intelligent Systems.

Allen-Bradley, "Bulletin 2803 VIM Vision Input Modul, Cat No. 2803-VIM2", 1991, Published in: US.

Allen-Bradley, "User's Manual, Bulletin 2803 VIM Vision Input Module, Cat. No. 2803-VIM1", 1987, Published in: US.

Allen-Bradley, "Bulletin 5370 CVIM Configuarable Vision Input Modul, User Manual Cat. No. 5370-CVIM", 1995, Published in: US.

Vision Solutions, "Captural Video Event Monitoring Solutions", p. 2, Publisher: EPIC Vision Solutions.

Pennwell Corporation, "CCD/CMOS Sensors Spot Niche Application", "Vision System Design—Imaging and Machine Vision Technology", 2004.

VisionSystems Design, "Cellular Device Processes At Ultrafast Speeds", Feb. 2003.

Di Mauro, et al, "Check—a generic and specific industrial inspection tool", "Vis. Image Signal Process", Aug. 27, 1996, pp. 241-249, vol. 143, No. 4, Publisher: IEEE Proc., Published in: Manchester, UK.

Wilson, "CMOS/CCD Sensors Spot Niche Applications", "Vision Systems Design", Jun. 2003.

Cognex Corporation, "3000/4000/5000 Image Processing, Revision 7.4 590-135 Edge Detection Tool", 1996.

Chen, Y.H., "Computer Vision for General Purpose Visual Inspection: a Fuzzy Logic Approach", "Optics and Lasers in Engineering 22", 1995, pp. 181-192, vol. 22, No. 3, Publisher: Elsevier Science Limited, Published in: Pokfulam, Hong Kong.

Wright, "Congachrome Vision System User's Guide, Newton Reserch Labs, Manual Edition 2.0, Documents Software Version 26.0", Jun. 3, 1996.

Keyence America, "CV-2100 Series", "High-Speed Digital Machine Vision System", Dec. 29, 2003, Publisher: http://www.keyence.com/products/vision/cv_2100_spec.html.

Cognex Corporation, "CVL Vision Tools Guide, Cognex MVS-8000 Series, Chapter 5, Symbol Tool, CVL 5.4", Dec. 1999.

Olympus Industrial, "Design Philosophy, I-Speed", 2002.

Cordin Company, "Electronic Imaging Systems, High Speed Imaging Solutions: 200-500 Series Camera", 2004, Publisher: www.cordin.com.

Photron, USA, "Product Information for Fastcam PCI", Copyright 2004, Publisher: www.photron.com.

Photron, USA, "Product Information for Fastcam-X 1280 PCI", Copyright 2004, Publisher: www.photron.com.

Chang, et al., "Feature Detection of Moving Images Using a Hierarchical Relaxation Method", "IEICE Trans. Inf. & Syst.", Jul. 7, 1996, vol. E79-D.

Stemmer Imaging GmbH, "Going Multimedia With Common Vision Blox, Product News", Feb. 20, 2003, Publisher: www.stemmer-imagin.de, http://www.imasys.fr/pages/news/item.php?view=319&item=313.

RVSI, "Hawkeye 1515—Smart Camera Reader for Directly Marked Data Matrix Codes", 2004, Published in: US.

Olympus Industrial, "High Speed, High Quality Imaging Systems, I-Speed Product Brochure", 2004, Publisher: Olympus Industrial.

Lavision GmbH, "High Speed CCD/CMOS Camera Systems, Overview of State-Of-The-Art High Speed Digital Camera Systems", "www.lavision.de", Sep. 24, 2004, Publisher: UltraSpeedStart.

Integrated Design Tools, "High-Speed CMOS Digital Camera, X-Stream Vision User's Manual", 2000.

IO Industries, Inc., "High Speed Digital Video Recording Software 4.0", 2002.

West, "High Speed, Real-Time Machine Vision", 2001, Publisher: Imagenation and Automated Vision Systems, Inc.

Asundi, et al., "High-Speed TDI Imaging for Peripheral Inspection", "Proc. SPIE, Machine Vision Applications in Industrial Inspection III", Mar. 1995, pp. 189-194, vol. 2423.

KSV Instruments Ltd., "HISIS 2002—High Speed Imaging System", 2004, Publisher: www.ksvltd.fi.

National Instruments, "IMAQVISION Builder Tutorial,", "http://www.ni.com/pdf/manuals/322228c.pdf", Dec. 2000, Publisher: IMAQ XP-002356530.

Rohr, "Incremental Recognition of Pedestrians From Image Sequences", "CVPR93", 1993.

Sick Industrial Sensors, "ICS 100—Intelligent Camera Sensor", "Sick Product Information".

Matrox Imaging, "Interactive Windows Imaging Software for Industrial and Scientific Applications, Inspector 4.0", Apr. 15, 2002, p. 8.

Adaptive Optics Associates, "10-K SEC Filing, IQ 180 Products", Dec. 2003.

Denis, "LabView and IMAQ Vision Builder Provide Automated Visual Test System", "XP00256529", 2001, p. 2, Publisher: LabVIEW, National Instruments, Published in: Ontario Canada.

Adaptive Optics Associates—Industrial Products and Systems, "Laser Scanning Product Guide", Mar. 2003, Publisher: Industrial Holographic and Conventional Laser 1D.

Baumberg, et al., "Learning Flexible Models From Image Sequences", "Research Rerport Series, Report 93.36", Oct. 1993, pp. 1-13, Publisher: University of Leeds, School of Computer Studies.

Matsushita Lightpix AE10, "NAiS Machine Vision", 2003, Publisher: Matsushita Machine Vision Systems.

National Semiconductor, "LM9630 100×128, 580 fps Ultra Sensitive Monochrome CMOS Image Sensor, Rev. 1.0", Jan. 2004, p. 21, Publisher: National Semiconductor Corporation.

Whelan, et al., "Machine Vision Algorithms in Java, Chapter 1—An Introduction to Machine Vision", "XP002480005", 2001, Publisher: Springer-Verlag.

Hunt, "Mastering Microsoft PhotoDraw 2000", May 21, 1999, Publisher: SYBEX, Inc.

Matsushita Imagecheckers, "NAiS Machine Vision", 2003, Publisher: Matsushita Machine Vision Systems.

Laser Scanning Product Guide, Adaptive Optics Associates, "Omnidirectional Bar Code Scanners", Mar. 2003, Publisher: Industrial Holographic and Conventional Laser 1D.

Corke, et al., "Real Time Industrial Machine Vision", "CSIRO Division of Manufacturing Technology", 1994, Publisher: Electrical Engineering Congress.

Uno, et al., "A Method of Real-Time Recognition of Moving Objects and Its Application", "Pattern Recognition", Nov. 11, 1975, pp. 201-208, vol. 8, Publisher: Pergamon Press, Published in: UK.

Cognex Corporation, "Screen Shot of the Checkmate GUI Ver. 1.6", Jan. 2005.

Cognex Corporation, "Sensorpart FA45 Vision Sensor", Sep. 29, 2006.

Siemens AG, "Simatic Machine Vision, Simatic VS 100 Series", Apr. 1, 2003, Publisher: www.siemens.com/machine-vision.

RVSI, "Smart Camera Reader for Directly Marked Data Matrix Codes, Hawkeye 1515 With GUI", 2004.

Visionx Inc., "SmartCapture Tool, Feature Fact Sheet", "www.visionxinc.com", 2003, pp. 1-25, Publisher: Visionx Inc., Published in: US.

Cognex Corporation, "4000/5000 SMD Placement Guidance Package, User's Manual, Release 3.8.00, Chapter 15, 590-6168", 1998.

IBM, "Software Controls for Automated Inspection Device Used to Check Interposer Buttons for Defects", Mar. 27, 2003, Publisher: IP.com Journal, IP.com, Inc.

(56) References Cited

OTHER PUBLICATIONS

Apple Computer Inc., "Studio Display User's Manual (online)", "Retrieved from the Internet: http://manuals.info.apple.com/en/StudioDisplay_15inchLCDUserManual.pdf", 1998.

Stauffer, et al., "Tracking-Based Automatic Object Recognition", pp. 133-134, Publisher: MIT, Artificial Intelligence Laboratory.

Photron, USA, "Product Information for Ultima 1024", Copyright 2004, Publisher: www.photron.com.

Photron, USA, "Product Information for Ultima 512", Copyright 2004, Publisher: www.photron.com.

Photron, USA, "Product Information for Ultima APX", Copyright 2004, Publisher: www.photron.com.

Zarandy, et al., "Ultra-High Frame Rate Focal Plane Image Sensor and Processor", "IEEE Sensors Journal", 2002, vol. 2, No. 6.

Cognex Corporation, "Cognex VisionPro, Getting Started—Quickstart Tutorial, 590-6560, Revision 3.5", May 2004, pp. 69-94.

Cognex Corporation, "VisionPro Getting Started, Revision 3.2, 590-6508", copyright 2003, Published in: US.

Zarandy, et al., "Vision Systems Based on the 128×128 Focal Plane Cellular Visual Microprocessor Chips", Mar. 2003, pp. III-518-III-521, Publisher: IEEE.

Hearing et al., "Visual Event Detection, Chapter 2, Section 8", 2001, Publisher: Kluwer Academic Publishers.

Demotte, "Visual Line Tracking", "Application Overview & Issues Machine Vision for Robot Guidance Workshop", May 5, 2004.

Cognex, Revision *3000/4000/5000 Programmable Vision Enginer, Vision Tools*, Revision 7.4, 590-0136 (1996) Chapter 4.

Bauer, Peter "Special Editiion Using Adobe Photoshop CS and Illustrator CS", *Indianapolis, IN: Que*. Published Mar. 2004. Accessed: Safari Tech Books Online. Web. Feb. 4, 2014. p. 283 and Chapters 9 and 28.

US 6,768,414, 07/2004, Francis (withdrawn)

* cited by examiner

SYSTEM, METHOD AND GRAPHICAL USER INTERFACE FOR DISPLAYING AND CONTROLLING VISION SYSTEM OPERATING PARAMETERS

RELATED APPLICATIONS

This application is a continuation-in-part of co-pending U.S. patent application Ser. No. 13/565,609, filed Aug. 2, 2012, entitled SYSTEM, METHOD AND GRAPHICAL USER INTERFACE FOR DISPLAYING AND CONTROLLING VISION SYSTEM OPERATING PARAMETERS, the entire disclosure of which is herein incorporated by reference, which is a continuation-in-part of U.S. patent application Ser. No. 12/758,455, filed Apr. 12, 2010, entitled SYSTEM AND METHOD FOR DISPLAYING AND USING NON-NUMERIC GRAPHIC ELEMENTS TO CONTROL AND MONITOR A VISION SYSTEM, the entire disclosure of which is herein incorporated by reference, which is a continuation of U.S. patent application Ser. No. 10/988,120, filed Nov. 12, 2004, entitled SYSTEM AND METHOD FOR DISPLAYING AND USING NON-NUMERIC GRAPHIC ELEMENTS TO CONTROL AND MONITOR A VISION SYSTEM, the entire disclosure of which is herein incorporated by reference.

FIELD OF THE INVENTION

The present invention relates to systems, methods and graphical user interface displays for determining whether an object or any portion thereof is present and/or at the correct position.

BACKGROUND OF THE INVENTION

Industrial manufacturing relies on automatic inspection of objects being manufactured. One form of automatic inspection that has been in common use for decades is based on optoelectronic technologies that use electromagnetic energy, usually infrared or visible light, photoelectric sensors (such as photodetectors), and some form of electronic decision making.

Machine vision systems avoid several disadvantages associated with conventional photodetectors. They can analyze patterns of brightness reflected from extended areas, easily handle many distinct features on the object, accommodate line changeovers through software systems and/or processes, and handle uncertain and variable object locations.

By way of example, FIG. 1 shows an illustrative embodiment of a vision detector 100 according to an illustrative embodiment for inspecting objects on a production line. A conveyor 102 transports objects to cause relative movement between the objects and the field of view (FOV) of vision detector 100. Objects 110, 112, 114, 116 and 118 are shown. In this example, the objects include exemplary features upon which location and inspection are based, including a label 120 and a hole 124. More particularly, the exemplary vision detector 100 detects the presence of an object by visual appearance and inspects it based on appropriate inspection criteria. If an object is defective (such as the label-less object 116), the vision detector 100 sends a signal via link 150 to a reject actuator 170 to remove the object (116) from the conveyor stream. An encoder 180 operatively related to the motion of the conveyor (or other relative motion) sends a signal 160 to the vision detector 100, which uses it to insure proper delay of signal 150 from the encoder count where the object crosses some fixed, imaginary reference point 190, called the mark point. If an encoder is not used, the delay can be based on time instead.

In an alternate example, the vision detector 100 sends signals to a PLC for various purposes, which may include controlling a reject actuator. In another exemplary implementation, suitable in extremely high-speed applications or where the vision detector cannot reliably detect the presence of an object, a photodetector is used to detect the presence of an object and sends a signal to the vision detector for that purpose. In yet another implementation, there are no discrete objects, but rather material flows past the vision detector continuously—for example a web. In this case the material is inspected continuously, and signals are sent by the vision detector to automation equipment, such as a PLC, as appropriate.

Basic to the function of the vision detector 100 is the ability to exploit the abilities of the imager's quick-frame-rate and low-resolution image capture to allow a large number of image frames of an object passing down the line to be captured and analyzed in real-time. Using these frames, the apparatus' on-board processor can decide when the object is present and use location information to analyze designated areas of interest on the object that must be present in a desired pattern for the object to "pass" inspection.

As the above-described systems become more advanced and available, users may be less familiar with all the settings and functions available to them.

Reference is made to FIG. 2 showing a block diagram of a vision detector 200 according to an illustrative embodiment. A digital signal processor (DSP) 201 runs software to control capture, analysis, reporting, HMI communications, and any other appropriate functions needed by the vision detector. The DSP 201 is interfaced to a memory 210, which includes high-speed random access memory for programs and data and non-volatile memory to hold programs and setup information when power is removed. The DSP 201 is also connected to an I/O module 220 that provides signals to automation equipment, an HMI interface 230, an illumination module 240, and an imager 220. A lens 250 focuses images onto the photosensitive elements of the imager 260.

The DSP 201 can be any device capable of digital computation, information storage, and interface to other digital elements, including but not limited to a general-purpose computer, a PLC, or a microprocessor. It is desirable that the DSP 201 be inexpensive but fast enough to handle a high frame rate. It is further desirable that it be capable of receiving and storing pixel data from the imager simultaneously with image analysis.

In the illustrative embodiment of FIG. 2, the DSP 201 is an ADSP-BF531 manufactured by Analog Devices of Norwood, Mass. An ADSP-BF53x would operate at a reduced level of performance compared to the ADSP-BF561 manufactured by Analog Devices of Norwood, Mass. In the illustrated arrangement, the Parallel Peripheral Interface (PPI) 270 of the ADSP-BF531 DSP 201 receives pixel data from the imager 260, and sends the data to memory controller 274 via Direct Memory Access (DMA) channel 272 for storage in memory 210. The use of the PPI 270 and DMA 972 allows, under appropriate software control, image capture to occur simultaneously with any other analysis performed by the DSP 201. Software instructions to control the PPI 270 and DMA 272 can be implemented by one of ordinary skill in the art following the programming instructions contained in the ADSP-BF533 Blackfin Processor Hardware Reference (part number 82-002005-01), and the Blackfin Processor Instruction Set Reference (part number 82-000410-14), both incorporated herein by reference. Note that the ADSP-BF531, and the compatible ADSP-BF532 and ADSP-BF533 devices, as well as the ADSP-BF561, have identical programming instructions and can be used interchangeably in this illustrative embodiment to obtain an appropriate price/performance tradeoff. The ADSP-BF532, ADSP-BF533 and ADSP-BF561 devices are substantially similar and have very similar peripheral support, for example, for the PPI and DMA.

The high frame rate desired by a vision detector suggests the use of an imager unlike those that have been used in prior art vision systems. It is desirable that the imager be unusually light-sensitive, so that it can operate with extremely short shutter times using inexpensive illumination. It is further desirable that it be able to digitize and transmit pixel data to the DSP far faster than prior art vision systems. It is moreover desirable that it be inexpensive and has a global shutter.

These objectives may be met by choosing an imager with much higher light sensitivity and lower resolution than those used by prior art vision systems. In the illustrative embodiment of FIG. 2, the imager 260 is an LM9630 manufactured by National Semiconductor of Santa Clara, Calif. The LM9630 has an array of 128.times.100 pixels, for a total of 12800 pixels, about 24 times fewer than typical prior art vision systems. The pixels are relatively large at approximately 20 microns square, providing high light sensitivity. The LM9630 can provide 500 frames per second when set for a 300-microsecond shutter time, and is sensitive enough (in most cases) to allow a 300-microsecond shutter using LED illumination. This resolution would be considered far too low for a vision system, but is quite sufficient for the feature detection tasks that are the objectives of the present invention. Electrical interface and software control of the LM9630 can be implemented by one of ordinary skill in the art following the instructions contained in the LM9630 Data Sheet, Rev 1.0, January 2004, which is incorporated herein by reference. In an illustrative embodiment, the imager 260 can also be an Aptina MTV024 imager which has an array of 752.times.480 pixels, for a total of 360960 pixels. This Aptina MTV024 imager has a reduced frame rate.

It is desirable that the illumination 240 be inexpensive and yet bright enough to allow short shutter times. In an illustrative embodiment, a bank of high-intensity red LEDs operating at 230 nanometers is used, for example the HLMP-ED25 manufactured by Agilent Technologies. In another embodiment, high-intensity white LEDs are used to implement desired illumination. In other embodiments, green and blue LEDs can be employed, as well as color filters that reject light wavelengths other than the wavelength(s) of interest.

In the illustrative embodiment of FIG. 2, the I/O module 220 provides output signals 222 and 224, and input signal 226. One such output signal can be used to provide a signal (150 in FIG. 1) for control of the reject actuator 170. Input signal 226 can be used to provide an external trigger.

As used herein an "image capture device" provides means to capture and store a digital image. In the illustrative embodiment of FIG. 2, the image capture device 280 collectively comprises a DSP 201, imager 260, memory 210, and associated electrical interfaces and software instructions. As used herein, an "analyzer" provides means for analysis of digital data, including but not limited to a digital image. In the illustrative embodiment, the analyzer 282 comprises a DSP 201, a memory 210, and associated electrical interfaces and software instructions. Also as used herein, an "output signaler" provides means to produce an output signal responsive to an analysis. In the illustrative embodiment, the output signaler 284 comprises an I/O module 220 and an output signal 222.

It will be understood by one of ordinary skill that there are many alternate arrangements, devices, and software instructions that could be used within the scope of the present invention to implement an image capture device 280, analyzer 282, and output signaler 284.

A variety of engineering tradeoffs can be made to provide efficient operation of an apparatus according to the present invention for a specific application. Consider the following definitions:

b fraction of the field of view (FOV) occupied by the portion of the object that contains the visible features to be inspected, determined by choosing the optical magnification of the lens 250 so as to achieve good use of the available resolution of imager 260;

e fraction of the FOV to be used as a margin of error;

n desired minimum number of frames in which each object will typically be seen;

s spacing between objects as a multiple of the FOV, generally determined by manufacturing conditions;

p object presentation rate, generally determined by manufacturing conditions;

m maximum fraction of the FOV that the object will move between successive frames, chosen based on above values; and r minimum frame rate, chosen based on above values.

From these definitions it can be seen that $$m \leq \frac{1-b-e}{n}$$

and $$r \geq \frac{sp}{m}$$

To achieve good use of the available resolution of the imager, it is desirable that b is at least 50%. For dynamic image analysis, n is desirably at least 2. Therefore, it is further desirable that the object moves no more than about one-quarter of the field of view between successive frames.

In an illustrative embodiment, reasonable values might be b=75%, e=5%, and n=4. This implies that m.ltoreq.5%, i.e. that one would choose a frame rate so that an object would move no more than about 5% of the FOV between frames. If manufacturing conditions were such that s=2, then the frame rate r would need to be at least approximately 40 times the object presentation rate p. To handle an object presentation rate of 5 Hz, which is fairly typical of industrial manufacturing, the desired frame rate would be at least around 200 Hz. This rate could be achieved using an LM9630 with at most a 3.3-millisecond shutter time, as long as the image analysis is arranged so as to fit within the 5-millisecond frame period. Using available technology, it would be feasible to achieve this rate using an imager containing up to about 40,000 pixels.

With the same illustrative embodiment and a higher object presentation rate of 12.5 Hz, the desired frame rate would be at least approximately 500 Hz. An LM9630 could handle this rate by using at most a 300-microsecond shutter. In another illustrative embodiment, one might choose b=75%, e=15%, and n=5, so that m.ltoreq.2%. With s=2 and p=5 Hz, the desired frame rate would again be at least approximately 500 Hz.

Having described the general architecture and operation of an exemplary vision system (vision Detector 200) that may support an HMI in accordance with an embodiment of this invention vision, reference is now made to FIG. 3, which shows a diagram of a Graphical User Interface (GUI) screen 300 for a Human-Machine Interface (HMI), interconnected with a vision detector (100) like that shown and described with reference to FIG. 1 above. The screen can reside on any acceptable HMI, including, but not limited to an Laptop Personal Computer (PC); Desktop PC, personal digital assistant or Notebook Computer (for example PC 194), cell phone, smart phone, or other appropriate device having an appropriate communication link (e.g. USB, wireless, network cable, etc.) with the vision detector (100). An appropriate HMI interface (described in connection with the above-incorporated-by-reference METHOD AND APPARATUS) interconnects with the exemplary vision detector's DSP to allow communication with the HMI. Note that the layout and menu contents of the illustrated screen 300 is exemplary, and a variety of layouts and menu items are contemplated in alternate embodiments. As described above, it is contemplated that the HMI is interconnected to the detector during setup and monitoring or testing. During normal runtime on a production line, the HMI may be disconnected and the detector freely operates various alarms, reject actuators (170) and other interconnected devices, while receiving optical inputs from illuminated objects and electronic inputs from line devices such as the encoder (180).

In this embodiment, the GUI 300 is provided as part of a programming application running on the HMI and receiving interface information from the vision detector. In the illustrative embodiment, a .NET framework, available From Microsoft Corporation of Redmond, Wash., is employed on the HMI to generate GUI screens. Appropriate formatted data is transferred over the link between the vision detector and HMI to create screen displays and populate screen data boxes, and transmit back selections made by the user on the GUI. Techniques for creating appropriate screens and transferring data between the HMI and vision detector's HMI interface should be clear to those of ordinary skill and are described in further detail below.

The screen 300 includes a status pane 302 in a column along the left side. This pane controls a current status box 304, the dialogs for controlling general setup 306, setup of object detection with Locators and Detectors 308, object inspection tool setup 310 and runtime/test controls 312. The screen 300 also includes a right-side column having a pane 320 with help buttons.

The lower center of the screen 300 contains a current selection control box 330. The title 332 of the box 330 relates to the selections in the status pane 302. In this example, the user has clicked select job 334 in the general setup box 306. Note, the general setup box also allows access to an item (336) for accessing a control box (not shown) that enables setup of the imager (also termed "camera"), which includes, entry of production line speed to determine shutter time and gain. In addition, the general setup box allows the user to set up a part trigger (item 338) via another control box (not shown). This may be an external trigger upon which the imager begins active capture and analysis of a moving object, or it may be an "internal" trigger in which the presence of a part is recognized due to analysis of a certain number of captured image frames (as a plurality of complete object image frames are captured within the imager's field of view).

The illustrated select job control box 330 allows the user to select from a menu 340 of job choices. In general, a job is either stored on an appropriate memory (PC or vision detector or is created as a new job. Once the user has selected either a stored job or a new job, the next button accesses a further screen with a Next button 342. These further control boxes can, by default, be the camera setup and trigger setup boxes described above.

Central to the screen 300 is the image view display 350, which is provided above the control box 330 and between the columns 302 and 320 (being similar to image view window 198 in FIG. 1). This display shows a current or stored image frame captured by the vision detector and, essentially, represents the vision detector's current field of view (FOV). In this example, an object 352 is approximately centered in the display. For the purposes of describing the illustrative embodiment, the exemplary object 352 is a bottle on a moving line having a main cylindrical body 354 having a narrowed upper cap section 356 with a series of graphics 358 thereon. Any acceptable object or pattern can be substituted herein and the relative motion between the object and the field of view can be generated by moving the objects, moving the vision detector (or moving its FOV) or moving both the objects and the vision detector. In this example, the object 352 is relative light in surface color/shade. While the background 360 is relatively dark (as depicted by dot shading), in general, there should exist sufficient contrast or shade differences between at least some portions of the object and the background to attain a basis for detecting and inspecting the object. However, it is contemplated that the object may be mostly dark and the background can be lighter in an alternate example.

As shown in FIG. 3, the object 352 is either a real-time image being returned from the vision detector under appropriate illumination or it is a stored image. In either case, the image in display 350 is the one upon which setup of the detector is performed. In this example, the object 352 is centered in the display 350 with background space on either side. In other examples, the object may be moved more closely to a side of the display, such as when detection and inspection are based upon internal features located at a distance from an edge.

Before describing further the procedure for manipulating and using the GUI and various non-numeric elements according to this invention, reference is made briefly to the bottom-most window 370 which includes a line of miniaturized image frames that comprise a so-called "film strip" of the current grouping of stored, captured image frames 372. These frames 372 each vary slightly in bottle position with respect to the FOV, as a result of the relative motion. The film strip is controlled by a control box 374 at the bottom of the left column.

Reference is now made to FIG. 4 showing a partial view of the diagram of the GUI display of FIG. 3, detailing an image view and associated control box with a cursor having automatically placed an edge-detecting locator of predetermined size and angle on the image view, and an exemplary threshold bar and setting slider within the control box, according to the illustrative embodiment. After performing other general setup functions (see box 306 in FIG. 3), the user may set up the mechanism for detecting the object 352 using the vision detector that is used herein as an example of a "vision system." The user clicks the setup detectors button 380 in FIG. 3 to access the control box 410. Within this box the user may decide which direction he or she wishes to have detection occur. The choices are machine or line-movement direction (typically horizontally or left-to right/right-to-left across the FOV) (button 450), cross direction (typically vertically or transverse to machine direction) (button 452) or angle direction (button 454). Once a direction is chosen for a main detector (note that additional directions may be chosen by accessing the control box 410 at a later time), the box 410 invites the user to click on a location in the object image, and that click generates a rectangular Locator ROI graphic 460 with an associated plunger 462 that fits to an adjacent edge of the object 352, as shown. A detailed description of an automated system and method for placing and sizing both Locators and Detectors is taught in commonly assigned U.S. Pat. No. 7,636,449, entitled SYSTEM AND METHOD FOR ASSIGNING ANALYSIS PARAMETERS TO A VISION DETECTOR USING A GRAPHICAL INTERFACE, the teachings of which are expressly incorporated herein by reference. The generalized threshold level is also set by the automated process based upon the overall difference between the light and dark pixels along the edge transition adjacent to the Locator 460. In brief summary, the threshold level determines how much transition along an edge or other feature is needed to turn the Locator "on."

In this example, when the user "clicks" on the cursor placement, the screen presents the control box 410, which now displays an operating parameter box 412. This operating parameter box 412 displays a single non-numeric parameter bar element 414 that reports threshold for the given Locator.

Once an object has been located within a field of view using the detectors of FIG. 4, it is typically desirable to apply certain tools to the object to determine certain qualitative features (i.e. label misplaced, etc.) without having to set up too many individual parameters and tests. For example, the width of a particular object is desired to be set during the training phase to train the system for the appropriate object width during run-time analysis. A caliper tool can be implemented in accordance with a prior art system. However, the user is required to expend effort and judgment during training. Some users desire a more automatic-automated option. The virtual caliper, although extremely useful, requires extensive user input and manual adjustment of individual operating parameters during training of an image.

SUMMARY OF THE INVENTION

A graphical user interface (GUI)-based system for generating and displaying vision system operating parameters employs automated contour sensor tools to determine whether a contour of interest is present or at the proper location within a scene. The operating parameters are automatically generated for the automated contour sensor tool, without requiring (free of) manual input from a user. The contour sensor tool can be a contour presence sensor that determines whether a contour is present in a scene (i.e. field of view of a vision detector) and a contour position sensor that determines whether a contour is at the proper position.

In an illustrative embodiment, an automatic region of interest graphic image is applied to a discrete region of a selected image in response to a single click ("one-click") by a user at the discrete region of the selected image. The image is selected by the user from a window on the GUI display containing a plurality of captured images of an object. An automated operating parameter is generated automatically in response to the single click by the user at a discrete region of the selected image when using the contour sensor tool, to determine whether a contour of interest is in the automated contour of interest graphic image. Illustratively, the automated region of interest graphic image is user-movable to allow the user to move the automated region of interest graphic image on the selected image, to thereby automatically reset the at least one automated operating parameter to a predetermined value in accordance with the positioning of the region of interest graphic image. For a contour position sensor, the pass-fail graphic is the region of interest graphic. For a contour presence sensor, the region of interest graphic comprises a contour bounding box.

More generally, the color of several graphics associated with a particular instance of a sensor indicate pass or fail. Red indicates fail, green indicates pass. The graphics associated with the presence sensor are: the region of interest graphic and contour graphic oriented at the best match and the search region graphic. The graphics associated with the position sensor are: the region of interest graphic and contour graphic oriented at the best match and the pass-fail region graphic. These graphics are shown in both phases of operation (setup or "training" and runtime).

In an illustrative embodiment, the automated contour of interest graphic image is applied by a contour tool searching for presence or position of a contour. At least one automated operating parameter for the contour presence tool is match threshold, angle tolerance, accuracy and feature size. At least one automated operating parameter for the contour position tool is match threshold, angle tolerance, accuracy and feature size.

Illustratively, a contour presence sensor computes the following measurements to determine whether a contour is present in the search region: X-location, Y-location, rotation, correlation score, and sensor match score. A contour position sensor computes the previous measurements, in addition to the following measurements to determine whether the contour of interest is in the pass-fail region: X-position score and Y-position score.

BRIEF DESCRIPTION OF THE DRAWINGS

The invention description below refers to the accompanying drawings, of which.

DETAILED DESCRIPTION

Figure 1:
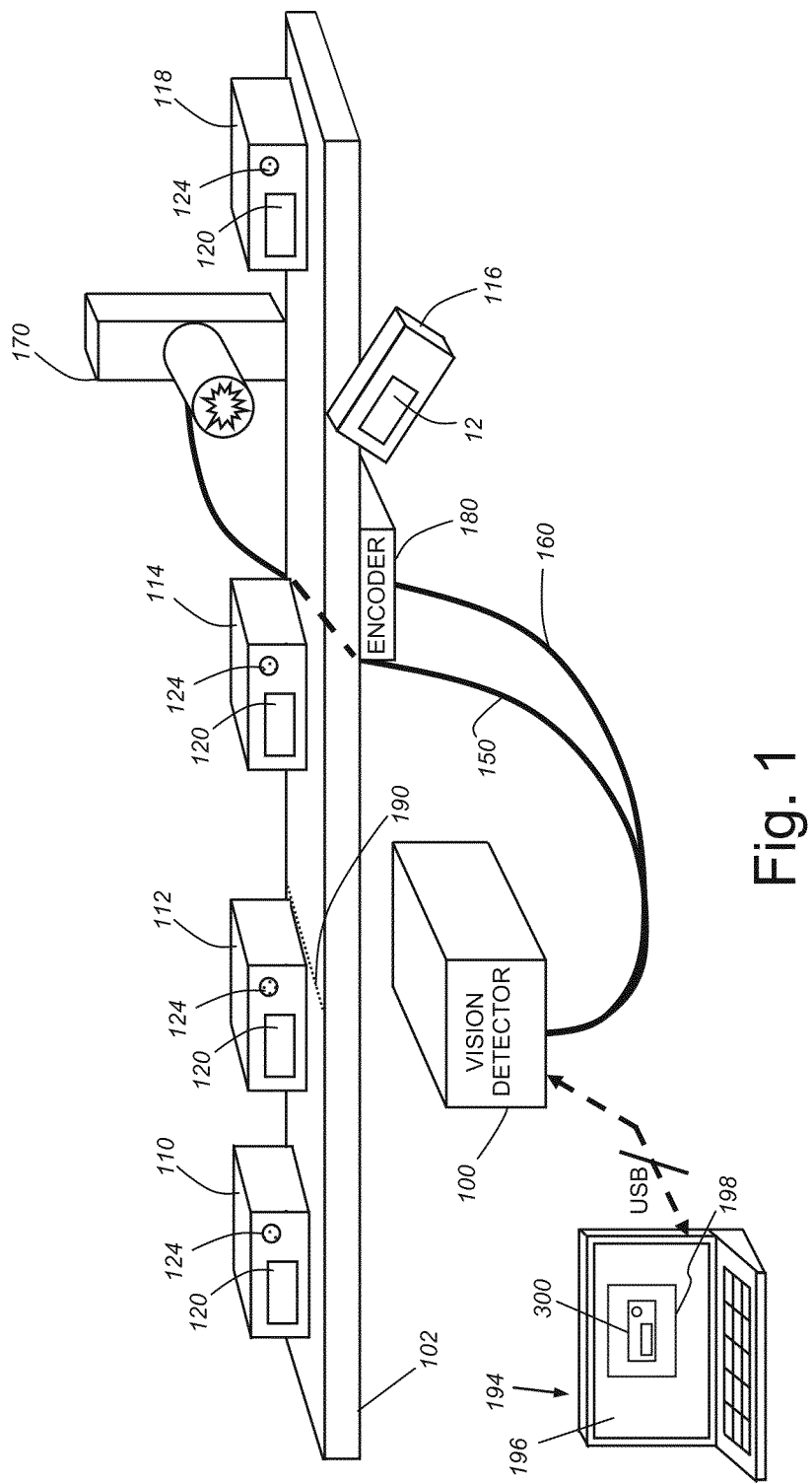
FIG. 1, already described, is a schematic diagram of an exemplary implementation of a vision detector, inspecting objects on a production line, according to a prior art illustrative embodiment.
Figure 2:
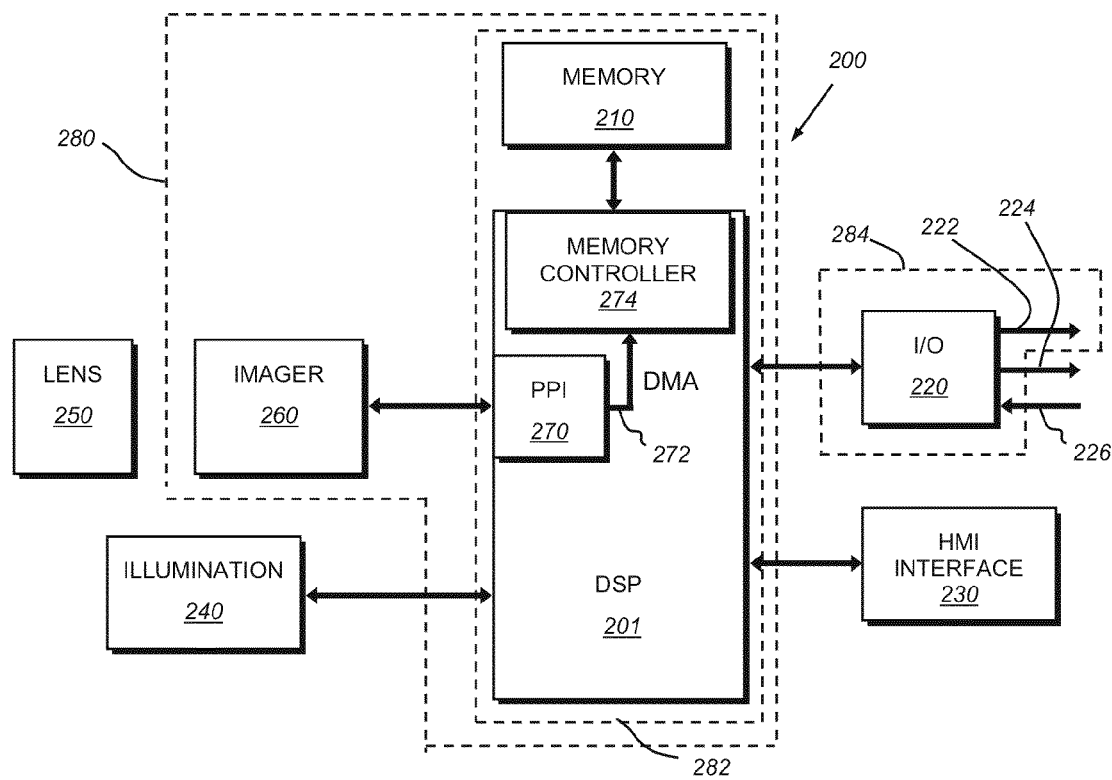
FIG. 2, already described, is a block diagram of an illustrative embodiment of a vision detector according to an illustrative embodiment.
Figure 3:
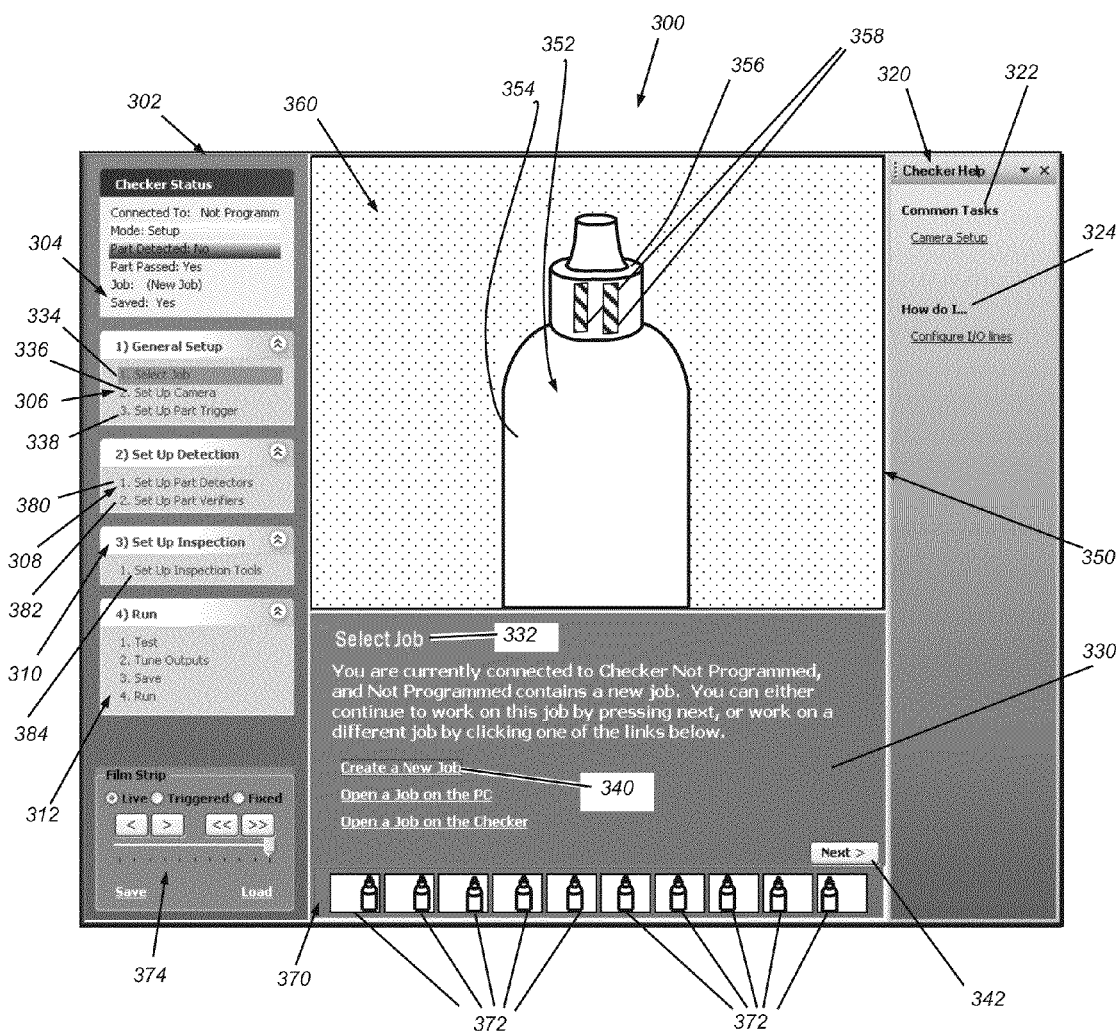
FIG. 3, already described, is a diagram of a graphical user interface (GUI) display for displaying and controlling vision detector operating parameters, according to an illustrative embodiment.
Figure 4:
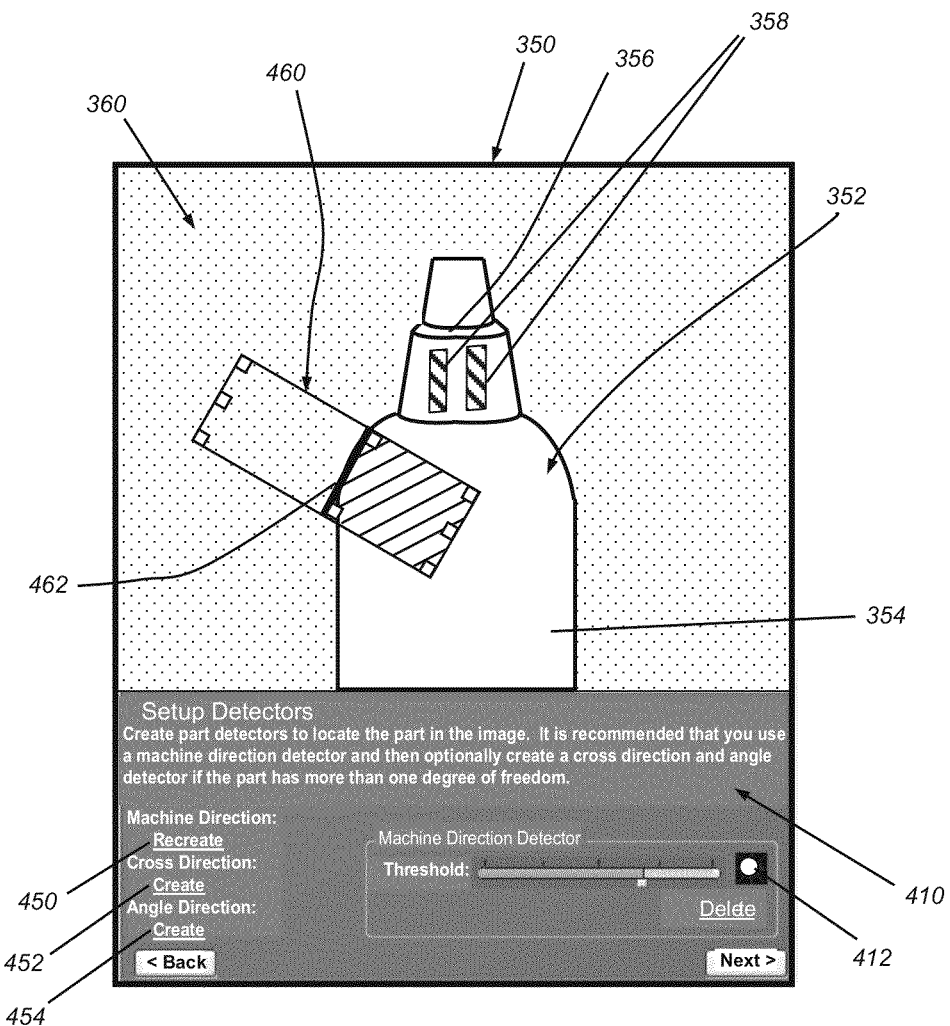
FIG. 4, already described, is a partial view of the diagram of the GUI display of FIG. 3, detailing an image view and associated control box with a cursor having automatically placed an edge-detecting Locator of predetermined size and angle on the image view, and an exemplary threshold bar and setting slider within the control box, according to the illustrative embodiment.

An automated position tool can be applied which advantageously verifies the position or presence of an object and yields a pass/field result, without (free of) requiring extensive parameter entry or user input. According to an illustrative embodiment, once a "part" or other object has been found using a part finding sensor, an automated graphic sensor can be applied. Illustratively, an automated graphic image is applied automatically to a discrete region of a selected image in response to a single (i.e. one) "click" by a user. By "click" it is generally meant a single activation operation by a user, such as the pressing of a mouse button or touch of another interface device, such as a touch screen. Alternatively, a click can define a set sequence of motions or operations. The manner of carrying out "click" is highly variable within ordinary skill to denote a single selection of a single location (a "discrete region") on a screen. The discrete region refers to the location on the selected image that a user "clicks" on (or otherwise selects), to apply a region of interest (ROI) graphic image thereto for detection and analysis of features of interest within the ROI graphic image. Also, a single "click" of the user refers to the selection of the discrete region by a user "clicking" or otherwise indicating a particular location to apply the ROI graphic image. The contour is found automatically based on the position of the one-click. The ROI graphic image is applied automatically in response to this single click and, advantageously, automatically generates the operating parameters associated with the ROI graphic image, without (free of) requiring manual input from a user.

Automated Contour Sensor Tools

Automated contour sensor tools can be implemented in accordance with the systems and methods herein for determining the presence or position of a contour within a scene. The contour sensors provide a search region for a presence sensor (or pass-fail region for a position sensor) as a bounding box surrounding the contour graphic image. The contour graphic image outlines the contour of interest to demonstrate where a contour of interest is in the automated ROI graphic image. As used herein, a "contour" refers to a collection of edges that together comprise a feature of interest. For example, a contour can comprise a large hole, the outline of a large hole or other feature of interest that comprise a collection of edges. The contour presence sensor searches for a contour pattern within a specified search region and within a specified angle range. Multiple candidates may be found, but the one candidate with the highest correlation score is selected by the contour presence sensor. The user can specify the search region, or it can be automatically set in response to "single-click" placement of the sensor. The contour position sensor likewise searches for a contour pattern within a search region and within a specified angle range. The search region for the contour position sensor also includes a pass-fail region. Multiple candidates may be found, but the one candidate with a passing position score and the highest correlation score is selected by the contour position sensor.

Figure 5:
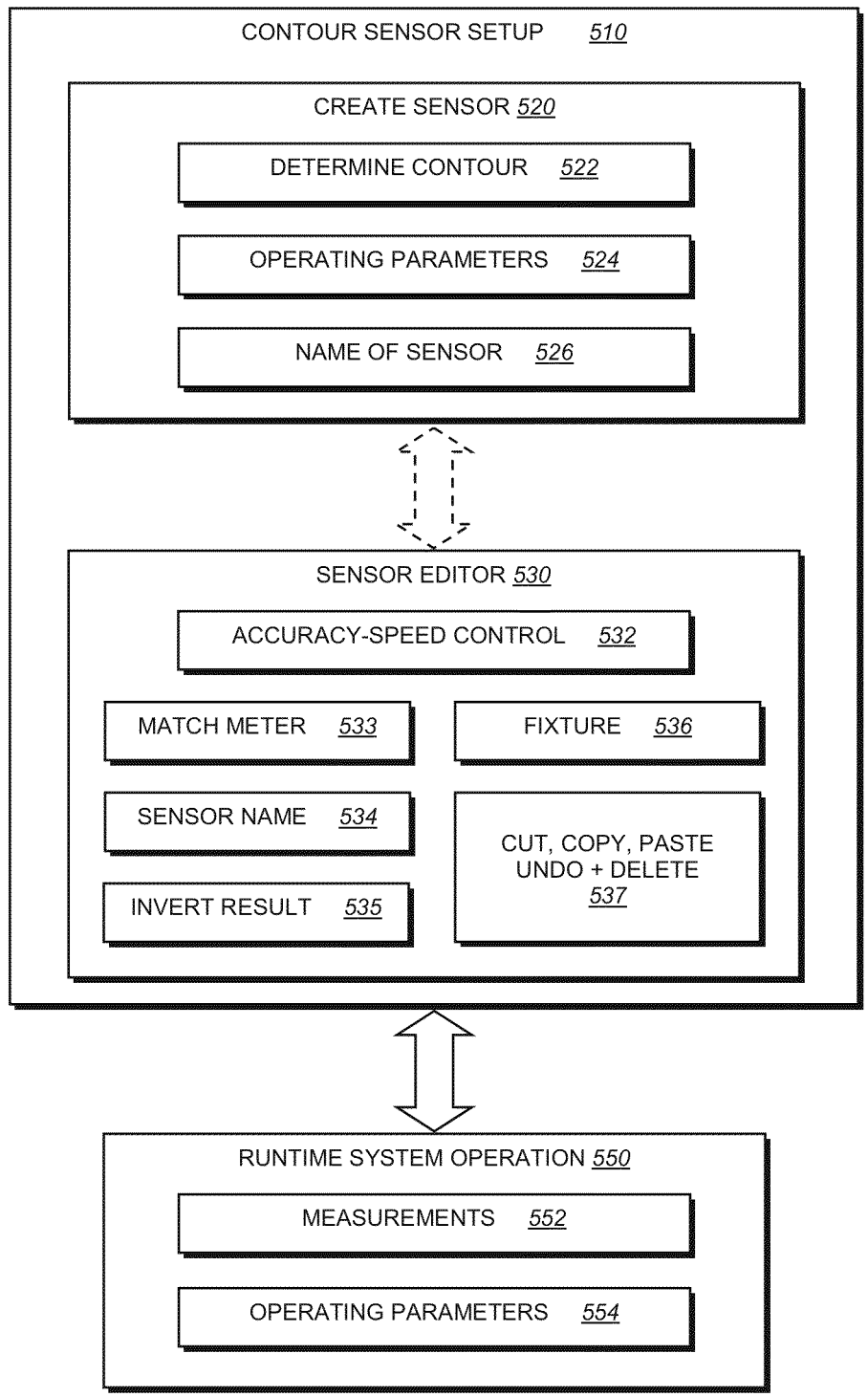
FIG. 5 is a block diagram showing the overall system flow for creating, editing and performing machine vision inspection using a contour sensor tool in accordance with an illustrative embodiment.

Reference is now made to FIG. 5 showing a block diagram of the overall system flow for creating, editing and performing machine vision inspection using a contour sensor tool in accordance with an illustrative embodiment. According to the illustrative embodiment, an automated contour graphic image is applied automatically to a discrete region of a selected image in response to a single "click" by a user proximate the discrete region on a graphical user interface. In this embodiment, the GUI 300 is provided as part of a programming application running on the HMI and receiving interface information from the vision detector. In the illustrative embodiment, a .NET framework, available From Microsoft Corporation of Redmond, Wash., is employed on the HMI to generate GUI screens. Appropriate formatted data is transferred over the (wired or wireless) link between the vision detector and HMI to create screen displays and populate screen data boxes, and transmit back selections made by the user on the GUI. Techniques for creating appropriate screens and transferring data between the HMI and vision detector's HMI interface should be clear to those of ordinary skill and are described in further detail below.

The contour sensor tool is applied to verify the position or presence of a contour and generate operating parameters automatically, according to an illustrative embodiment. The system desirably provides a pass or fail result based upon whether the operating parameters indicate that a contour is located within a region of interest graphic image. In various vision procedures, it is desirable, once an object has been located, to determine certain qualitative features of the object, to indicate whether a defect is present by verifying the position (or presence) of a feature of interest, such as a contour. It is desirable to provide a graphical pass-fail region to a user to determine the correct position (or presence) of items, by first creating a sensor and then using the sensor during runtime system operation. The runtime system operation refers to the vision detector environment for inspecting objects on a production line, for example as shown and described herein with reference to FIG. 1. The part (object) is found, then the contour sensor is applied.

Referring back to FIG. 5, in a machine vision system there is generally a training or "setup" phase, which occurs prior to runtime inspection of objects, and a runtime phase during which objects are inspected. The setup phase is shown in exemplary screen displays in FIGS. 9-11, and the runtime phase is shown in the exemplary screen display of FIG. 12. With continued reference to FIG. 5, the contour sensor setup 510 occurs during the training phase and includes a create sensor module 520 and a sensor editor 530. Creating a contour sensor includes determining the contour 522, determining the operating parameters 524 and providing a name for the sensor 526. The sensor can then optionally be edited using a sensor editor 530 having a plurality of controls that can be manipulated on a graphical user interface (GUI) by a user to determine whether a particular training image results in a pass result (i.e. the contour is present or at the correct position) or a fail result (i.e. the contour is not present or not at the correct position). The "accuracy-speed control" 532 allows the user to optimize system performance, such as a sensitivity slider to control distortion tolerance and an accuracy slider to control search granularity. If certain controls require retraining, the original contour image is used for retraining. The match meter 533 is employed by the user to determine if the best scoring contour in the scene ("field of view") produces a pass or a fail result. The "sensor name" 534 provides a text box showing the sensor name. The sensor is automatically given a name (such as "ContourPresencen", where n is the number assigned by the system, and the user can change the sensor name by typing into the sensor name text box.

The "invert result" 535 is a checkbox that can be provided to the user on the GUI to invert the sense of the pass-fail result. The pass-fail result is usually given by: PF=Match Score>+ threshold.

When invert result is enabled, PF!=PF

Accordingly, the result is inverted so that a "pass" result becomes a failing result, and likewise a "fail" result becomes a passing result. This can be particularly useful when searching for a contour and it is desirable to know when the contour is not present (pass when not present), but the sensor is setup to detect for the presence of the contour. Thus, a "pass" result will indicate that the contour is present, where it is in fact desirable for the result to be a failing result. This, inverting the result would be beneficial in this result so that an object "fails" if the contour is present.

A fixture button 536 can also be provided, which is typically disabled unless a part finding sensor has been created. If it has been selected, it can be indicated by a color such as yellow. The default value is "selected" and it is automatically selected if a part finding sensor is created after the Contour Sensor has been created. When selected, the sensor location tracks the location of the part finder sensor; otherwise the location is always at the point set during setup mode (510). The sensor editor 530 can also include standard cut, copy, paste, undo and delete operations 537. In an illustrative embodiment the "CTRL+Z" function (pressing the "control" (CTRL) key and the "Z" key simultaneously) can be used to undo any modification to the sensor and, more specifically, any change to the job. When the user uses CTRL+V to paste, a new sensor is advantageously created that is identical to the one on the clipboard, except that it is automatically assigned a new name in accordance with the embodiments herein.

During runtime system operation 550, the contour sensor computes measurements 552. In an illustrative embodiment, for a contour presence sensor, the measurements include X-location, Y-location, rotation, correlation score (typically internally visible within the system) and sensor match score (visible to the user). These presence sensor measurements are made available to the user and the correlation score is used to determine whether the contour is present in the search region. For a contour position sensor, the measurements include all of the measurements for the contour presence sensor, and additionally include an X-position score and a Y-position score. The position sensor measurements determine whether the contour is at the correct position within the pass-fail region. There are a variety of operating parameters 554 that affect contour selection and gradient computation during training, and searching granularity at runtime. Most parameters are set to reasonable defaults or automatically computed by the system. The remainder are set by the user via the system GUI control. In certain embodiments, the parameters are all set automatically to reasonable thresholds by the system, and can be further edited by the user through the sensor editor (530 for example). The parameters include match threshold, angle tolerance, accuracy and feature size.

General Operation—Contour Presence Sensor and Contour Position Sensor

The contour presence sensor searches for a contour pattern within its specified search region and within the specified angle range. Multiple candidates can be found, but the one with the highest correlation score is selected by the contour presence sensor. The search region can be specified by the user. The contour position sensor likewise searches for a contour pattern within a search region and within a specified angle range. The search region for the contour position sensor includes a pass-fail region. Multiple candidates may be found, but the one candidate with a passing position score and the highest correlation score is selected by the contour position sensor.

Pass-Fail Criteria

Each location in the search region is checked for a contour match. The sensor will pass if any match score is greater or equal to the accept threshold set by the user.

Contour Region

The contour region refers to the region of the image from which the contour pattern was extracted. The contour region can be shown graphically on the image (training image or runtime image) and manipulated during setup mode.

Search Region

The search region specifies the region of the image that the sensor examines for contour candidates. The contour candidate must fall completely within the search region in order to be found. The location of the search region is set either by a part-finding sensor or by the trained location if there is no part-finding sensor. The auto-placement or part-finder can locate the sensor such that the search region is located partially off the image. When the sensor is run, the effective search region is constrained to lie on the image and is clipped if necessary.

The search region can impose a minimum constraint of approximately 8 pixels longer in width and 8 pixels longer in height than the contour region in an exemplary embodiment. During the one-click process the search region (for the presence sensor) and the pass-fail region (for the position sensor) are automatically calculated to allow rotation of the contour region plus a certain amount for tolerance.

In addition to the features above, the contour position sensor includes the following features:

Pass-Fail Region

The region is generally designated by a rectangle, and its location is set by the part finding sensor or by the trained location. Either auto-placement or the part-finder can locate the sensor such that the pass-fail region is located partially off the image. In these cases, the user can drag the region, but it may not be resized unless it is fully on the image. The reported position of the passing (or failing) contour is specified by the center of the contour bounding box. The bounding box size and location can advantageously be used for both pass-fail decisions and user-drawn graphics.

Graphically, the user can select the sensor by clicking on the pass-fail region displayed on the image. This causes the editor panel for that sensor to be opened. The user can then reposition the region by dragging and can change the size using the size handles on the corners. The pass-fail region is displayed in a predetermined color (such as yellow) when the sensor has been selected; otherwise the color is red or green depending on the output pass-fail status for the position sensor.

Search Region

The search region specifies the region of the image that the sensor examines for contour candidates. The contour candidate must fall completely within the search region in order to be located within the scene. The sensor searches a region of the image that includes the pass-fail region expanded by the representative contour dimensions. If the trained contour is found outside the pass-fail region for the position sensor but touches it, it is found, a potential candidate, and can be displayed. Given that the match score is independent of rotation, the search region size is determined by padding on all sides by the contour bounding box diagonal. The diagonal is a simple approximation of the contour diameter. Either auto-placement or the part-finder can locate the sensor such that the search region is located partially off the image. When the sensor is run, the effective search region is constrained to lie on the image and is clipped if necessary.

Single-Click Automatic Placement of Contour Sensor

The single-click automatic placement allows a user to create a contour sensor using a PC mouse (or other input such as touch screen tap or touch, or other single selection) of a location ("discrete region") on an image associated with the object of interest. The single-click automatic placement is applicable to both the contour presence sensor and the contour position sensor.

Figure 6:
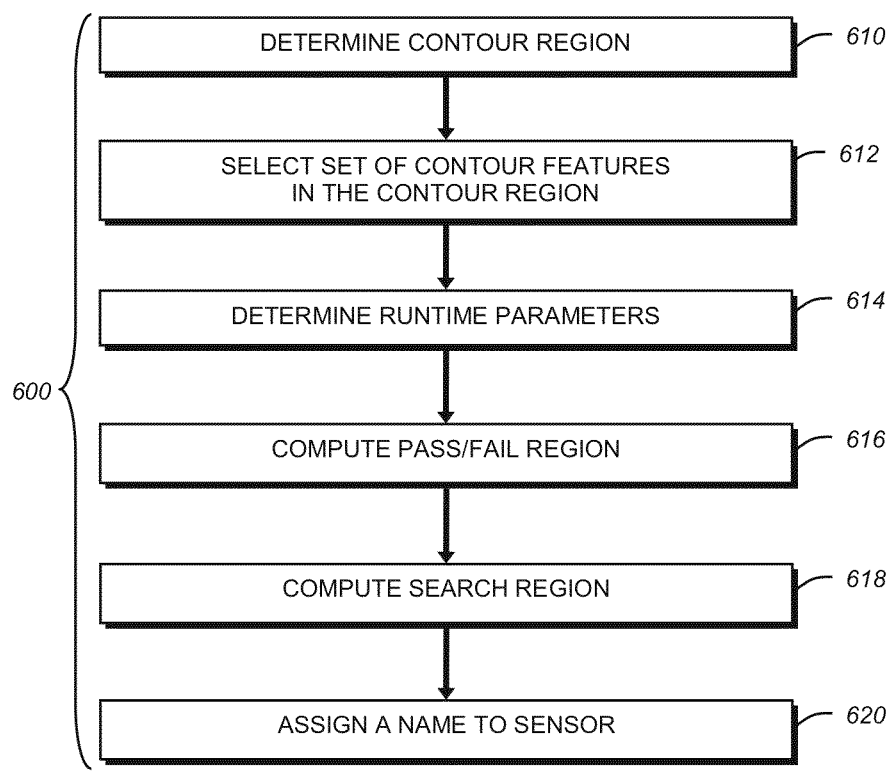
FIG. 6 is a flow chart of a procedure for single-click automatic placement of a contour sensor, in accordance with the illustrative embodiment.

Reference is now made to FIG. 6 showing a flow chart of a procedure 600 for single-click automatic placement of a contour sensor, in accordance with an illustrative embodiment. The procedure 600 for one-click auto placement of a contour sensor commences at step 610 by determining the contour region. As stated hereinabove, the contour region is the region of the image from which the contour pattern was extracted. At step 612, the procedure then selects a set of contour features in the contour region. The runtime parameters that will optimize runtime search performance are determined at step 614. A nominal pass-fail region is computed at step 616 (for the position sensor), and a search region is computed at step 618. As described hereinabove, the pass-fail region refers to a location at which the match score is greater or equal to the accept threshold, and the search region specifies the region of the image that the sensor examines for contour candidates. At step 620, a name is assigned to the sensor.

If the single-click automatic placement procedure fails to produce a satisfactory contour, the user has the option of manually placing the sensor, editing the contour, or deleting the sensor and trying again.

The image region that is used to produce the contour is stored in the "job", meaning a particular instance (or instances) of a machine vision inspection. Frequently a job comprises a machine vision inspection of a particular object or type of object. When the job is loaded, the image is restored and the contour is reproduced from the image. This is flexible in that a mask image can be created at a later stage. Mask images created by the user can be saved and restored.

Contour Presence Sensor: Single-Click Placement

Figure 7:
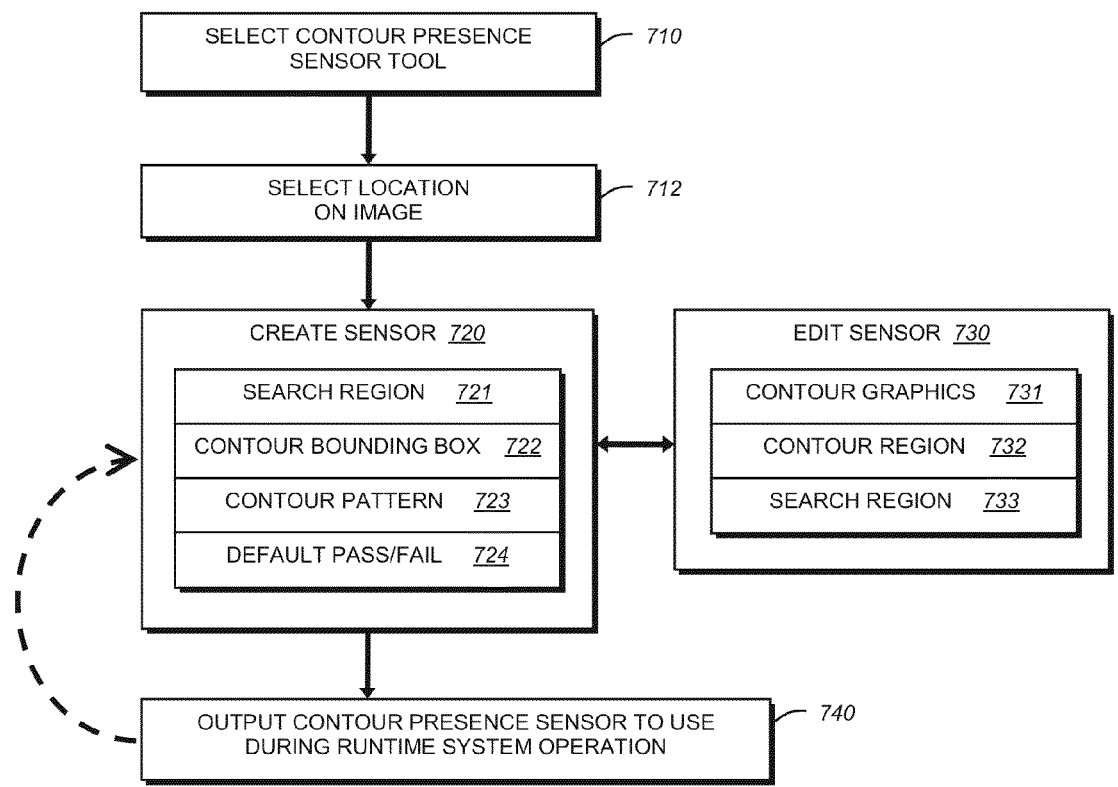
FIG. 7 is a flow chart of a procedure for creating a contour presence sensor to determine whether a contour is present within a field of view, in accordance with an illustrative embodiment.

Reference is now made to FIG. 7 showing a flow chart of a procedure for creating a contour presence sensor to determine whether a contour is present within a field of view, in accordance with an illustrative embodiment. To create a contour presence sensor, the user first selects a part inspection button in the setup panel (see, for example, the "Inspect My Part" button 934 in FIG. 9 herein). The user then selects the contour sensor tool at step 710 which begins a single-placement dialog. The user can then select a location on the image at step 712 that is contained by the object. Alternatively, a user can click the "cancel" button to cancel the job. If a point (location) on the image is selected, the machine vision system creates the sensor 720 by analyzing the region proximate the point and presents a search region 721, contour bounding box 722, representative contour pattern 723 and default pass-fail threshold 724. Refer, for example, to FIG. 10 showing a search region 1040 and contour region ("contour bounding box") 1030 and contour pattern graphics 1020 in accordance with an exemplary graphical illustration. The contour pattern is drawn on the image by coloring the pixels corresponding to the object boundaries in a particular color (such as green, as shown by the dashed line 1020 in FIG. 10). The edit sensor module 730 includes editing the contour graphics 731, contour region 732 and search region 733 as appropriate to provide the desired pass-fail result under runtime system operation of machine vision inspection. The output contour presence sensor is used during runtime system operation at step 740 and can be created or edited as appropriate to provide desired pass-fail results. The user sets a pass-fail threshold for a contour "match score" which is returned by the searching operation. The match score value is in the range of 0-100.

The search region constructed around the representative contour is centered at the contour bounding box center. The constructed search region (for example 1040 in FIG. 10) is large enough to accommodate the contour bounding box (for example 1030 in FIG. 10) at any rotation.

The location of the contour sensor is at the center of the contour bounding box described above, regardless of (independent of) the current orientation of the contour pattern.

The single-click placement also creates a name for the sensor in the form of, for example, "ContourPresencen" where n is a number assigned by the machine vision system.

Certain areas in a scene can cause the single-click placement to fail, including scenes with no features and objects with poor contrast. When placement fails, default contour and search regions are shown, but no contour pattern is displayed. A user is given two options: to manually place the contour using the contour region control, or delete the sensor and create a new one on another part of the scene. The user can then improve the scene contrast by going back to the setup image step.

Contour Presence Sensor: Manual Placement

Once a representative contour has been found, it can be replaced by moving or resizing the contour region box that is displayed on the image. Illustratively, any contour editing changes made to the previous contour are lost if the contour region is moved or resized.

The search region box tracks the contour region box after it has been moved, so that the search region is in the same relative location. If this causes the sensor region to fall of the image, then the sensor region is clipped or otherwise cropped to fit.

Contour Position Sensor: Single-Click Placement

Figure 8:
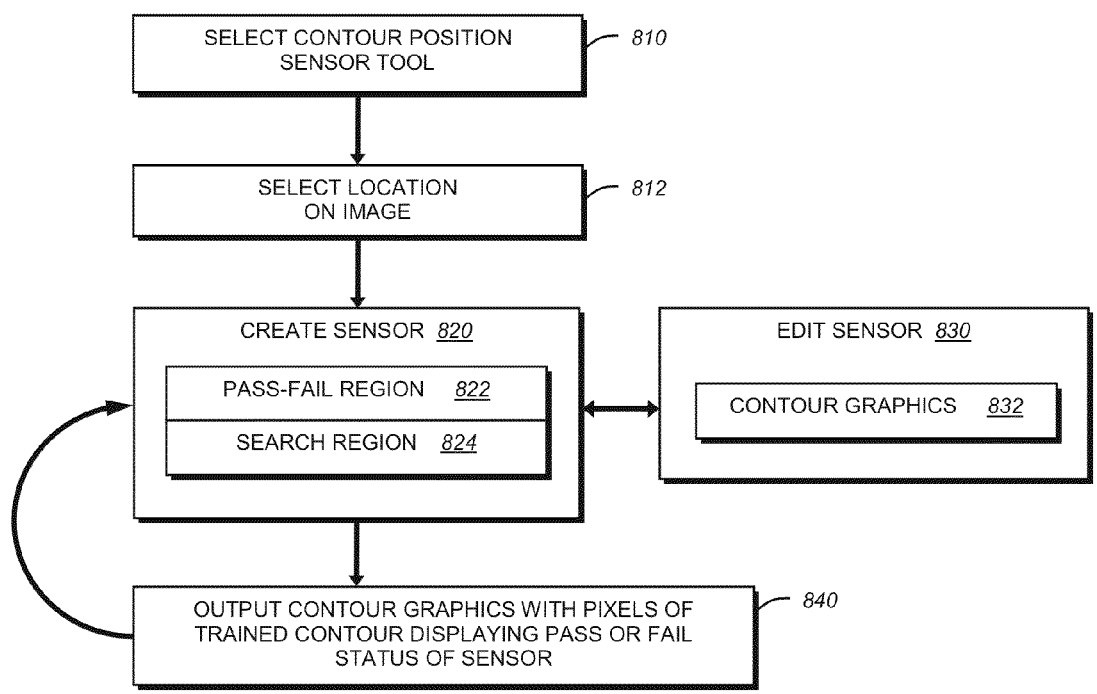
FIG. 8 is a flow chart of a procedure for creating a contour position sensor to determine whether a contour is at a proper position within a field of view, in accordance with an illustrative embodiment.

Reference is now made to FIG. 8 showing a flow chart of a procedure for creating a contour position sensor to determine whether a contour is at a proper position within a field of view, in accordance with an illustrative embodiment. To create a contour position sensor, the user first selects a part inspection button in the setup panel (see, for example, the "Inspect My Part" button 934 in FIG. 9 herein). The user then selects the contour position sensor tool at step 810 which begins a single-placement dialog. The user can then select a location on the image at step 812 that is contained by the object. Alternatively, a user can click the "cancel" button to cancel the job. If a point (location) on the image is selected, the machine vision system creates the sensor 820 by analyzing the region proximate the point and presents a pass-fail region 822, contour bounding box, representative contour pattern and default pass-fail threshold. The contour pattern is drawn on the image by coloring the pixels corresponding to the object boundaries in a particular color (such as green, as shown by the dashed line 1020 in FIG. 10). The edit sensor module 830 includes editing the contour graphics 832 as appropriate to provide the desired pass-fail result under runtime system operation of machine vision inspection. The output contour position sensor is used during runtime system operation at step 840. The bounding box of the candidate contour is used to compute the position score in runtime operation to provide the pass-fail results. The location of each of the four edges of the box is compared to the locations of the vertical or horizontal boundaries of the pass fail region. A linear scoring method is used in which the score is "50" if the edge touches a boundary, decreases to 0 as it moves outside the boundaries by half the pass-fail region size and increases to 100 as it moves within the boundaries by half the pass-fail region size. The worst of the four scores is the final score. The pass-fail threshold is set to 50. Toggle button controls available on the GUI allow the user to disregard the horizontal edges or vertical edges. Both controls may be used together to disable position checking completely.

The pass-fail region 822 is constructed around the representative contour and is centered at the contour bounding box center. Illustratively, it is a square whose size is equal to approximately 1.5 times the bounding box diagonal.

The search region 824, which is not visible to the user, is also centered at the contour bounding box center. Illustratively, it is a square which is 2.5 times the bounding box diagonal. This allows finding all good contour matches that might contact the pass-fail region.

The location of the contour sensor is at the center of the minimum box described hereinabove, regardless of (independent of) the current orientation of the contour pattern.

The single click placement also creates a name for the sensor in the form of "ContourPositionn" where n is a number assigned by the machine vision system.

Certain areas in a scene can cause the single-click placement to fail, including scenes with no features and objects with poor contrast. When placement fails, default contour and pass-fail regions are shown, but no contour pattern is displayed. A user is given two options: to manually place the contour using the contour region control, or delete the sensor and create a new one on another part of the scene. The user can choose to first improve the scene contrast by going back to the setup image step.

Contour Position Sensor: Manual Placement

Once a representative contour has been found, it can be replaced by moving or resizing the contour region box that is displayed on the image. Illustratively, any contour editing changes made to the previous contour are lost if the contour region is moved or resized.

EXEMPLARY EMBODIMENT

Contour Presence Sensor: Editing

Figure 9:
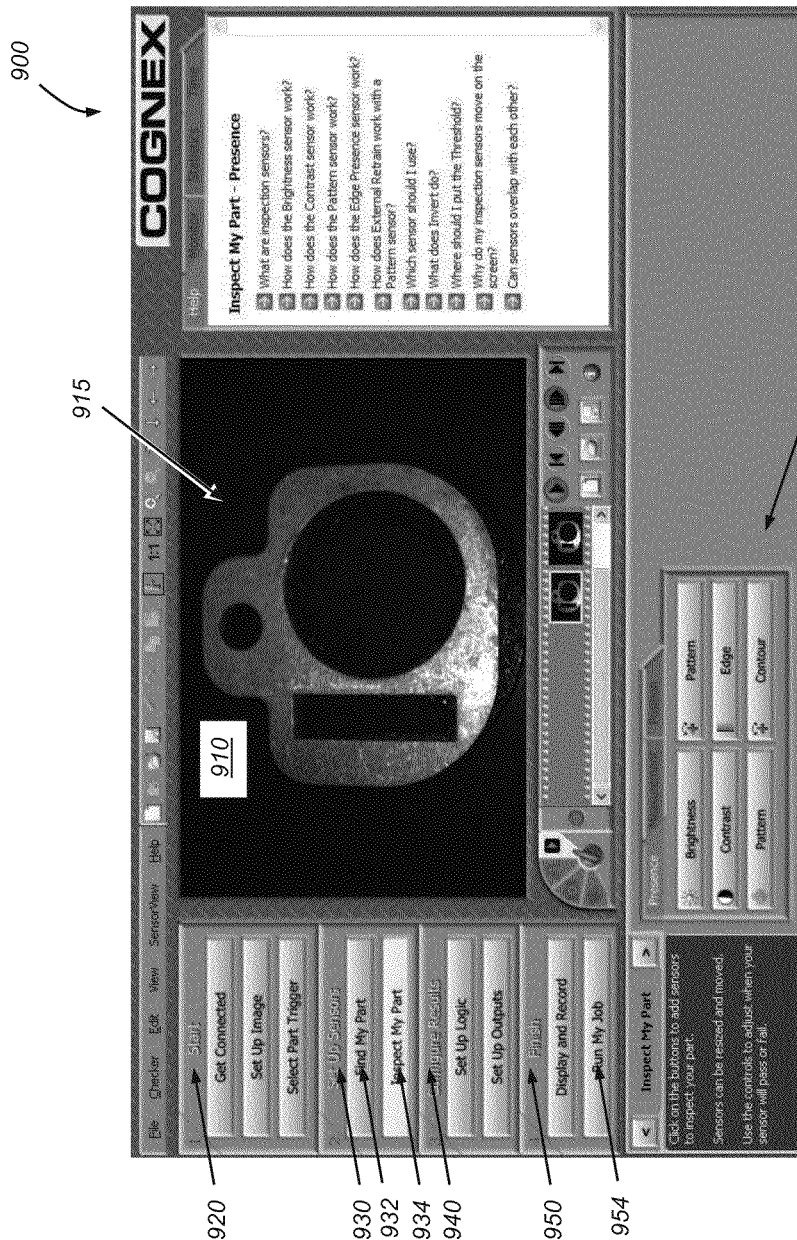
FIG. 9 is a diagram of a graphical user interface (GUI) display for creating a contour sensor during training of a machine vision system, in accordance with an illustrative embodiment.
Figure 10:
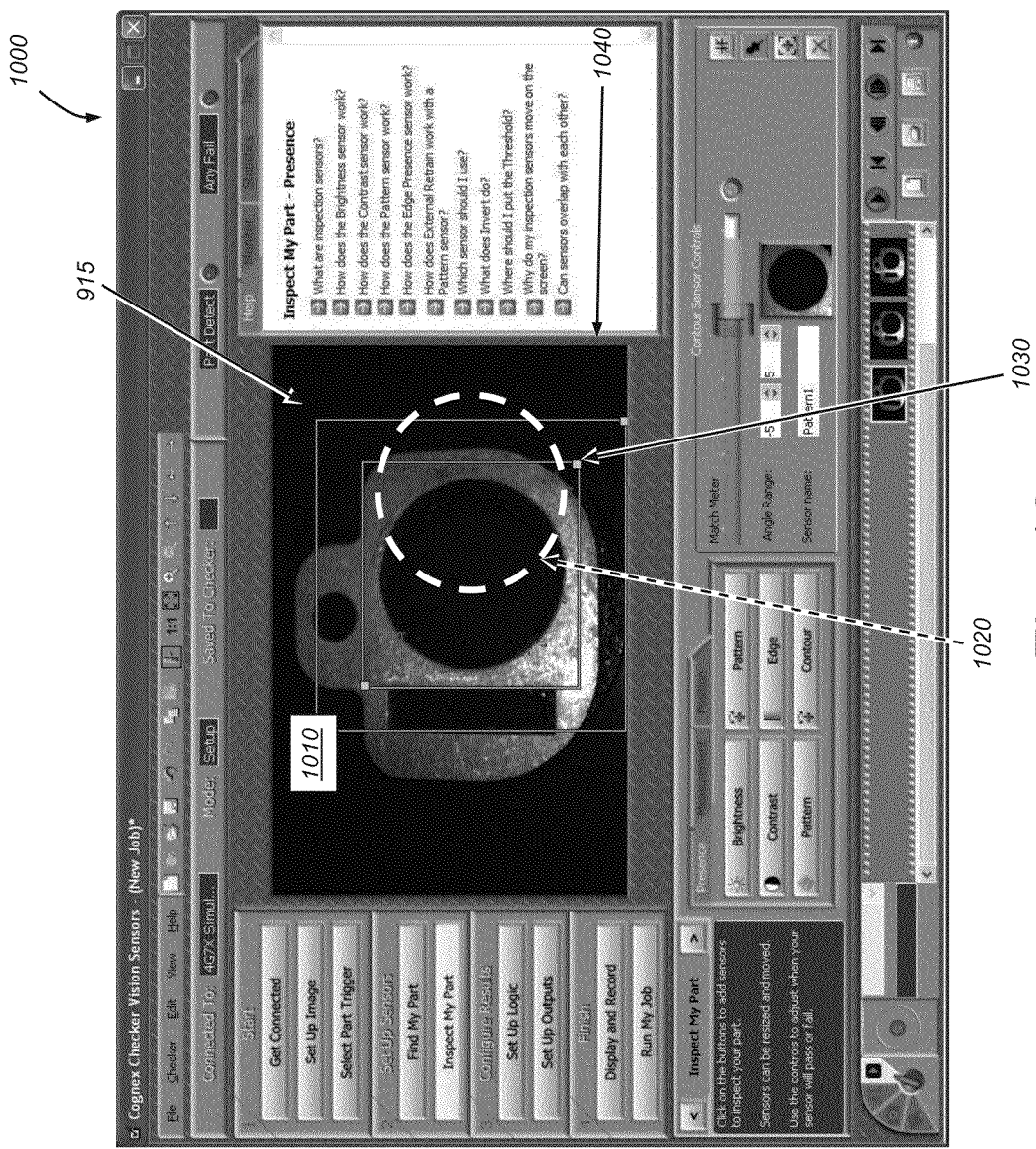
FIG. 10 is a diagram of a GUI display for editing the contour sensor during training of the machine vision system, in accordance with the illustrative embodiment.

Reference is now made to FIGS. 9-12 showing exemplary diagrams of GUI displays for creating and editing a contour sensor for use in machine vision inspection of objects, in accordance with an illustrative embodiment. FIG. 9 is a diagram 900 of an exemplary graphical user interface (GUI) display for creating a contour sensor during training of a machine vision system, according to an illustrative embodiment. An image 910 of an object 915 to be inspected is shown on the screen 900. The object 915 in the image is similar in appearance to the objects to be inspected during runtime machine vision inspection. On the display, the user has the option to "start" vision system setup 920, to set up sensors 930, configure results 940 or finish 950. A user can set up sensors 930 by selecting a "Find My Part" button 932 or an "Inspect My Part" button 934. Once in the "inspect my part" section of the set up sensors phase, a user can select the "Contour Presence" button 936 to initiate creating a contour presence sensor. Once the "Contour" button 936 has been selected, a user can click at any location on the image 910 in which a contour of interest on the object 915 is to be inspected. Once a user selects a particular contour (for example the larger hole in the image 1010) on the feature 915, the user views an illustrative screen as shown in exemplary diagram 1000 which shows contour graphics 1020, outlining the contour of interest, the contour region 1030 and the search region 1040. In an exemplary embodiment, the contour region is approximately 300 pixels×300 pixels, but is variable within ordinary skill and can be 316×304 pixels in an exemplary embodiment, and also variable depending upon the particular application and part being inspected. The search region can be slightly larger (for example 8 pixels wider and 8 pixels taller) to allow for slight movement within the field of view and other tolerances during inspection. The editing panel 1050 allows user to make certain modifications to the sensor if desired, however it is shown that the operating parameters are provided automatically in response to the user selecting a contour of interest in the image 910. When the sensor is selected, the search region box and the contour bounding box can be displayed in a predetermined color of interest, such as yellow. To open the editor panel for a sensor, the machine vision system must be in setup mode, and the user must be at the "Inspect My Part" step of the job.

In training, the system finds regions 1020 and 1030 and constructs 1040. Then during runtime operation, the system searches for 1020 within 1040 to determine whether a contour is present or at the correct position. The box 1030 can be dragged and dropped by the user to the desired contour.

The search region 1040 can be repositioned by the user by dragging the perimeter and the size can be changed using the size handles on the corners of the search region. The search region 1040 minimum size is constrained by slightly larger (8 pixels in both directions) than the contour bounding box. The user can reposition the contour region 1030 by dragging the perimeter and can change the size using the size handles on the corners. Changing the location or size of the contour region causes the sensor to create a new contour pattern.

Alternatively, the user can enable and display the contour region by selecting a toggle control on the sensor panel. The contour region can be displayed on the image as a grey, filled box with size handles. The contour region is only shown when the sensor is selected and the toggle control is enabled. The region is displayed as a filled box to make it obvious to the user that manipulating it can have destructive consequences.

The pixels of the trained contour are drawn in either green (pass) or red (fail), or other color combinations are highly variable, depending upon the sensor output pass-fail status. The contour is drawn at the location of the best match in the search region (see, for example, 1020 in FIG. 10).

Figure 11:
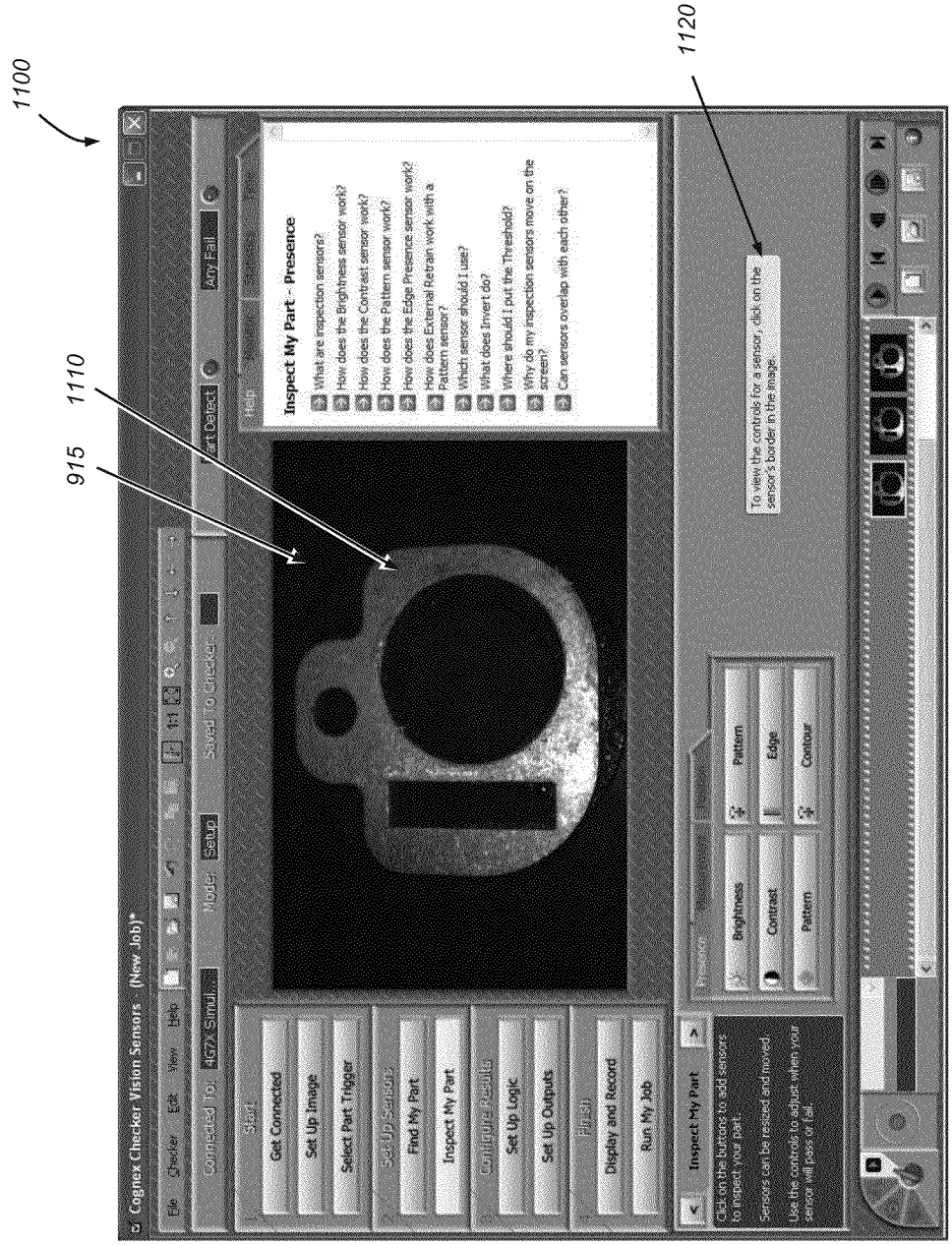
FIG. 11 is a diagram of a GUI display showing the training image after the sensor has been created, with the sensor being "unselected", in accordance with the illustrative embodiment.
Figure 12:
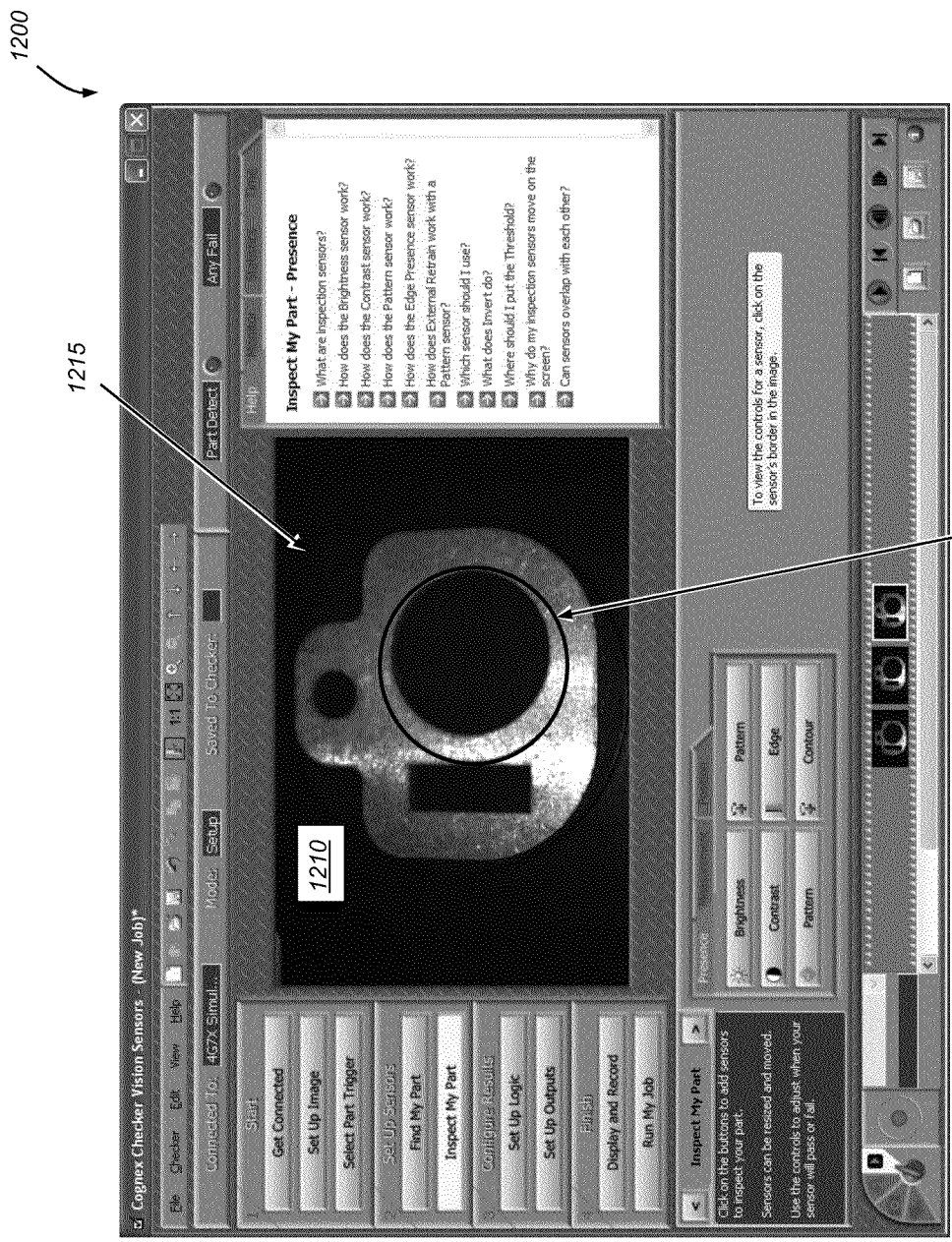
FIG. 12 is a diagram of a GUI display showing run mode graphics of a failed sensor for a contour presence sensor tool. In accordance with the illustrative embodiment.

Reference is now made to FIG. 11 showing an exemplary screen display 1100 of the training image after the sensor has been created, with the sensor being "unselected", in accordance with an illustrative embodiment. A user can select the sensor by clicking on the vicinity of the contour graphics 1110. In FIG. 11, the sensor is shown in the "unselected state", and as shown by message 1120, "to view the controls for a sensor, click on the sensor's border in the image". FIG. 12 is a diagram of a GUI display 1200 showing the run mode graphics of a failed sensor for a contour presence sensor. As shown, the object 1215 of the image 1210 is not contained completely within the contour graphics 1220 and, thus, the object 1215 fails the contour presence sensor.

It should now be clear that the above-described systems, methods, GUIs and automated position tools affords all users a highly effective vehicle for setting parameters to determine whether a feature of interest is at the correct position, such as a feature presence or position, cap or label position, component placement, or other applications known in the art. The illustrative above-described systems, methods, and GUIs, are applicable to those of skill to determine whether a feature of interest (such as a contour) is at the correct position, through use of a region of interest graphic image and associated operating parameters that are automatically generated.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. For example, while a moving line with objects that pass under a stationary inspection station is shown, it is expressly contemplated that the station can move over an object or surface or that both the station and objects can be in motion. Thus, taken broadly the objects and the inspection station are in "relative" motion with respect to each other. Also, while the above-described "interface" (also termed a "vision system interface") is shown as a single application consisting of a plurality of interface screen displays for configuration of both trigger logic and main inspection processes, it is expressly contemplated that the trigger logic or other vision system functions can be configured using a separate application and/or a single or set of interface screens that are accessed and manipulated by a user separately from the inspection interface. The term "interface" should be taken broadly to include a plurality of separate applications or interface screen sets. In addition, while the vision system typically performs trigger logic with respect to objects in relative motion with respect to the field of view, the objects can be substantially stationary with respect to the field of view (for example, stopping in the filed of view). Likewise, the term "screen" as used herein can refer to the image presented to a user which allows one or more functions to be performed and/or information related to the vision system and objects to be displayed. For example a screen can be a GUI window, a drop-down box, a control panel and the like. It should also be clear that the various interface functions and vision system operations described herein controlled by these functions can be programmed using conventional programming techniques known to those of ordinary skill to achieve the above-described, novel trigger mode and functions provided thereby. In general, the various novel software functions and operations described herein can be implemented using programming techniques and environments known to those of skill. Likewise, the depicted novel GUI displays, while highly variable in presentation and appearance in alternate embodiments, can also be implemented using tools and environments known to those of skill. Accordingly, this description is meant to be taken only by way of example, and not to otherwise limit the scope of this invention.

What is claimed is:

1. A machine vision system including a processor,
the processor displays a graphical user interface (GUI) and controls vision system operating parameters of a contour position sensor, the GUI comprising:
an automated region of interest (ROI) graphic image that is applied to a discrete region of a selected image of an object in response to a single click by a user at the discrete region of the selected image, the selected image being selected by the user from a window on the GUI display containing a plurality of captured images of the object;
at least one automated operating parameter that is generated automatically in response to the single click by the user at the discrete region of the selected image to determine whether a contour of interest is in the automated ROI graphic image; and
a contour graphic image that outlines the contour of interest to demonstrate whether the contour of interest is within the automated ROI graphic image.

2. The GUI display as set forth in claim 1 wherein the contour sensor comprises a contour presence sensor and is generated automatically in response to the single click by the user to determine whether a contour is present in the automated ROI graphic image, the automated ROI graphic image comprising a contour region for the contour presence sensor, and the GUI display further comprising a search region that specifies the region of the selected image that the sensor examines for contour candidates.

3. The GUI display as set forth in claim 2 wherein the contour region comprises a bounding box that surrounds the contour of interest.

4. The GUI display as set forth in claim 2 wherein measurements computed by the contour presence sensor to determine whether the contour is present in the search region comprise at least one of: X-location, Y-location, rotation, correlation score and sensor match score.

5. The GUI display as set forth in claim 2 wherein the contour graphics for the contour presence sensor are drawn at a location of the best match in the search region.

6. The GUI display as set forth in claim 1 wherein the contour sensor comprises a contour position sensor and is generated automatically in response to the single click by the user to determine whether a contour is at a correct position within the automated ROI graphic image, the automated ROI graphic image comprising a contour region for the contour position sensor, the GUI display further comprising a pass-fail region for the contour position sensor that is centered at boundaries of the contour of interest.

7. The GUI display as set forth in claim 6 wherein measurements computed by the contour position sensor to determine whether the contour is at the correct position within the pass-fail region comprise at least one of: X-location, Y-location, rotation, correlation score, sensor match score, X-position score and Y-position score.

8. The GUI display as set forth in claim 6 wherein the contour graphics for the contour position sensor are drawn at a location of the best candidate selected by the contour position sensor.

9. The GUI display as set forth in claim 1 wherein the contour graphic image is drawn as pixels of the contour of interest in a first color for a passing contour that is in the search region and a second color for a failing contour that is not in the search region.

10. The GUI display as set forth in claim 1 further comprising an indicator graphic that indicates whether the contour of interest is in the pass-fail region.

11. The GUI display as set forth in claim 1 wherein the automated ROI graphic image is applied in response to the single click by the user by:
determining a contour region;
selecting a set of contour features in the contour region; 5
determining runtime parameters;
computing a pass-fail region;
computing a search region; and
assigning a name to the contour sensor.

12. A machine vision system including a processor,
the processor displays a graphical user interface (GUI) and controls vision system operating parameters of a contour position sensor, the GUI comprising:

a contour region graphic image applied to a discrete region of a selected image of an object in response to a single click by a user at the discrete region of the selected image, the selected image selected by the user from a window on the GUI display containing a plurality of captured images of the object;

a search region that specifies a region of the selected image that the contour presence sensor examines for contour candidates;

at least one automated operating parameter that is generated automatically in response to the single click by the user at the discrete region of the selected image to determine whether a contour of interest is in the contour region graphic image; and a contour graphic image that outlines the contour of interest to demonstrate whether the contour of interest is present within the contour region graphic image.

13. The GUI display as set forth in claim 12 wherein the contour region comprises an area of approximately 300 pixels by 300 pixels.

14. The GUI display as set forth in claim 12 wherein the search region is approximately 8 pixels longer in width and 8 pixels longer in height than the contour 3 region.

15. The GUI display as set forth in claim 12 wherein the contour graphic image comprises pixels of a trained contour that are drawn at a location of the best match in the search region on the selected image in a first color for a passing contour and a second color for a failing contour.

16. The GUI display as set forth in claim 12 wherein the automated ROI graphic image is applied in response to the single click by the user by:
  determining a contour region;
  selecting a set of contour features in the contour region;
  determining runtime parameters;
  computing a search region; and
  assigning a name to the contour sensor.

17. A machine vision system including a processor,
  the processor displays a graphical user interface (GUI) and controls vision system operating parameters of a contour position sensor, the GUI comprising:
    a contour region graphic image applied to a discrete region of a selected image in response to a single click by a user at the discrete region of the selected image, the selected image selected by the user from a window on the GUI display containing a plurality of captured images of the object;
    a pass-fail region for the contour position sensor that is centered at the boundaries of the contour to determine if a contour of interest is at a correct position within the contour region graphic image;
    at least one automated operating parameter that is generated automatically in response to the single click by the user at the discrete region of the selected image to determine whether the contour of interest is in the contour region graphic image; and
    a contour graphic image that outlines the contour of interest to demonstrate whether the contour of interest is at the correct position within the contour region graphic image.

18. The GUI display as set forth in claim 17 wherein the pass-fail region is based on 2 the size of the contour region.

19. The GUI display as set forth in claim 17 wherein the contour region is approximately 300 pixels by 300 pixels.

20. The GUI display as set forth in claim 17 wherein the contour graphic image comprises pixels of a trained contour that are drawn at a location of the best candidate selected by the contour position sensor on the selected image in a first color for a passing 4 contour and a second color for a failing contour.

21. The GUI display as set forth in claim 17 wherein the automated ROI graphic image is applied in response to the single click by the user by:
  determining a contour region;
  selecting a set of contour features in the contour region;
  determining runtime parameters;
  computing a pass-fail region;
  computing a search region; and
  assigning a name to the contour sensor.

* * * * *